(12) United States Patent
Franco

(10) Patent No.: US 10,281,478 B2
(45) Date of Patent: *May 7, 2019

(54) COMBINATION GROWTH FACTOR THERAPY AND CELL THERAPY FOR TREATMENT OF ACUTE AND CHRONIC DISEASES OF THE ORGANS

(71) Applicant: Wayne P. Franco, Middletown, CT (US)

(72) Inventor: Wayne P. Franco, Middletown, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/637,807

(22) Filed: Jun. 29, 2017

(65) Prior Publication Data

US 2018/0017577 A1    Jan. 18, 2018

Related U.S. Application Data

(63) Continuation-in-part of application No. 12/798,220, filed on Mar. 31, 2010, now Pat. No. 9,694,038.

(51) Int. Cl.
| | |
|---|---|
| A61K 35/28 | (2015.01) |
| A61K 35/51 | (2015.01) |
| G01N 33/68 | (2006.01) |
| A61K 38/18 | (2006.01) |
| A61K 35/30 | (2015.01) |
| A61K 35/32 | (2015.01) |
| A61K 35/50 | (2015.01) |
| C12N 5/0775 | (2010.01) |

(52) U.S. Cl.
CPC ......... *G01N 33/6893* (2013.01); *A61K 35/28* (2013.01); *A61K 35/30* (2013.01); *A61K 35/32* (2013.01); *A61K 35/50* (2013.01); *A61K 35/51* (2013.01); *A61K 38/1825* (2013.01); *A61K 38/1866* (2013.01); *C12N 5/0665* (2013.01); *G01N 2800/32* (2013.01); *G01N 2800/324* (2013.01)

(58) Field of Classification Search
CPC ... A61K 2035/124; A61K 35/28; A61K 35/51
See application file for complete search history.

(56) References Cited

U.S. PATENT DOCUMENTS

| | | | | |
|---|---|---|---|---|
| 5,980,887 | A | 11/1999 | Isner et al. | 424/93.7 |
| 6,805,860 | B1 | 10/2004 | Alt | 424/93.7 |
| 7,811,557 | B1* | 10/2010 | Kraus | A61K 35/14 424/93.1 |
| 2002/0061587 | A1 | 5/2002 | Anversa | 435/366 |
| 2004/0018174 | A1 | 1/2004 | Palasis | 424/93.7 |
| 2004/0037811 | A1 | 2/2004 | Penn et al. | 424/93.7 |
| 2004/0131585 | A1 | 7/2004 | Itescu | 424/85.1 |
| 2004/0161412 | A1 | 8/2004 | Penn et al. | 424/93.7 |
| 2004/0191215 | A1 | 9/2004 | Froix et al. | 424/85.1 |
| 2004/0258670 | A1* | 12/2004 | Laughlin | A61K 35/28 424/93.21 |
| 2007/0110727 | A1* | 5/2007 | Kang | C12N 5/0607 424/93.7 |

FOREIGN PATENT DOCUMENTS

| | | | | |
|---|---|---|---|---|
| DE | 19940012 | 3/2001 | | C12N 15/79 |
| WO | WO1994028916 | 12/1994 | | A61K 37/02 |
| WO | WO2004014302 | 2/2004 | | |

OTHER PUBLICATIONS

Yan et al, CNS Neurosci Ther. Oct. 2014;20(10):935-944 (Year: 2014).*
Haller et al., Biol. Blood Marrow Transplant. Jul. 2013; 19(7): 10 (Year: 2013).*
Yang et al., Int J Stem Cells. May 2013;6(1):37-44 (Year: 2013).*
Cardiovasc Radiat Med. Jul.-Dec. 2002; 3(3-4): -172-5. Accession PMID: 12974369; "Different Growth Conditions for Peripherial Blood Endothelial Progenitors".
Exp Hematol. Jun. 2000; 28(6): 700-6. Accession PMID: 10880756; "Expression and Secretion of Vascular Endothelial Growth Factor-A by Cytokine-Stimulated Hematopoietic progenitor cells. Possible role in the Hematopoietic Microenvironment".
Ann N Y Acad Sci. Apr. 30, 1999; 872:176-85; discussion 185-6. Accession PMID:10372121; Regulation of Transendothelial Migration of Hematopoietic Progenitor Cells.
Blood. Feb. 15, 1999;93(4):1253-63. Accession PMID:9949168; "Maturation of Embryonic Stem Cells into Endothelial Cells in an in Vitro Model".
Stem Cells. 1998;16 Suppl 1:159-65. Accession PMID: 11012158; "The Role of Endothelium in the Regulation of Hematopoietic Stem Cell Migration".
Hum Cell. Mar. 1997;10(1):45-50. Accession PMID: 9234064; "Human Mesenchymal Stem Cells Respond to Fibroblast Growth Factors".

* cited by examiner

Primary Examiner — Daniel C Gamett

(57) ABSTRACT

Ischemia is treated to prevent or manage disease by delivering stem cells derived from cord blood and/or tissue. A patient suffering from disease caused in at least some part by ischemia is selected. At least one dose consisting of an effective amount of stem cells is administrated through intravenous (IV), intra thecal, intra-arterial, via catheter into the organ, via Myostar catheter into the heart, intracoronary, intrapericardial, and/or by direct injection into the organ. Effectiveness of the administration is monitored at selected time periods to determine whether there exists an improved clinical indication. A second dose is administered by a method that is at least invasive as that utilized in the prior dose, and the steps are repeated until the clinical indication shows improvement or until there is contraindication to continued treatment. Diseases include at least one of Ischemia, arteriosclerosis, complications of ischemia, decreased perfusion, aging or diabetes.

28 Claims, 3 Drawing Sheets

Specification includes a Sequence Listing.

SEQUENCE LISTING

```
<160> NUMBER OF SEQ ID NOS: 4

<210> SEQ ID NO 1
<211> LENGTH: 27
<212> TYPE: DNA
<213> ORGANISM: Homo sapiens

<400> SEQUENCE: 1
cagtgtccaa catgctgctg gaaattg                                           27

<210> SEQ ID NO 2
<211> LENGTH: 22
<212> TYPE: DNA
<213> ORGANISM: Homo sapiens

<400> SEQUENCE: 2
taaaggtctt cttggtgatg cc                                                22

<210> SEQ ID NO 3
<211> LENGTH: 17
<212> TYPE: DNA
<213> ORGANISM: Homo sapiens

<400> SEQUENCE: 3
gcctcgctct ggaaaga                                                      17
```

```
<210> SEQ ID NO 4
<211> LENGTH: 17
<212> TYPE: DNA
<213> ORGANISM: Homo sapiens

<400> SEQUENCE: 4
tccatgcaga caacctt                                                17
```

COMBINATION GROWTH FACTOR THERAPY AND CELL THERAPY FOR TREATMENT OF ACUTE AND CHRONIC DISEASES OF THE ORGANS

CROSS-REFERENCE TO RELATED APPLICATION

This is a Continuation-In-Part of application Ser. No. 12/798,220, filed Mar. 31, 2010, now U.S. Pat. No. 9,694,038 issued Jul. 4, 2017.

BACKGROUND OF THE INVENTION

1. Field of the Invention

The present invention uses cord blood and or tissue derived stem cells to prevent, lesson, or delay ischemia or the complications of ischemia, including but not limited to stroke, Myocardial Infarction (MI), aging, diabetes, and critical limb ischemia.

2. Description of the Prior Art

There are many different diseases of the organs that affect the population. Included in those diseases, are ones affecting the heart. Chronic myocardial ischemia is the leading cardiac illness affecting the general population in the Western world. Since the occurrence of angina symptoms or objective physiological manifestations of myocardial ischemia signifies a mismatch between myocardial oxygen demand and the available coronary blood flow. The goal of therapy is to restore this balance. This can be achieved either by attempting to prevent further disease progression through modification of risk factors, or by more aggressive modes of therapy such as reducing the myocardial oxygen demand (i.e. reducing the heart rate, myocardial contractility or blood pressure) by using anti-anginal medications, or by restoring the blood supply by means of mechanical interventions such as percutaneous transluminal angioplasty or its variants, or coronary artery bypass surgery, coronary angioplasty (PTCA) or bypass surgery (CABG).

Many tissues in the body fail to regenerate independently after injury or other environmental stresses, and intervention may be required to restore function to those tissues. Organs including the brain, spinal cord, pancreas, liver, kidney, muscle, and upper and lower gastrointestinal tracts are unable to adequately repair after the onset of certain diseases. Similarly, the intrinsic repair mechanisms of the heart are often inadequate to restore function after a myocardial infarction. Thus, destroyed cardiomyocytes are not effectively replaced. The remaining cardiomyocytes are unable to reconstitute tissue lost to necrosis, and heart function deteriorates over time.

Recent attempts to ameliorate the damage caused by myocardial infarction or other disease processes have been directed to regenerating myocardial tissue by implanting a variety of stem and progenitor cells that can differentiate into cardiac muscle. Adult-derived bone marrow cells have been shown to regenerate cardiomyocytes following an infarction. Similar studies have been directed to other organs of the body.

Stem cells have the capacity, upon division, for both self-renewal and differentiation into progenitors. Thus, dividing stem cells generate both additional primitive stem cells and somewhat more differentiated progenitor cells. In addition to the well-known role of stem cells in the development of blood cells, stem cells also give rise to cells found in other tissues, including but not limited to the brain, spinal cord, pancreas, liver, kidney, muscle, and upper and lower gastrointestinal tracts.

Stem cells have the ability to divide indefinitely, and to specialize into specific types of cells. Due to the regenerative properties of stem cells, they have been considered an untapped resource for potential engineering of tissues and organs. It would be a major advancement in science to provide uses of stem cells with respect to addressing acute and chronic diseases of the organs.

Angiogenesis is a complex process that involves endothelial cell migration and proliferation, extracellular matrix breakdown, attraction of pericytes and macrophages, smooth muscle cell proliferation and migration, formation and "sealing" of new vascular structures, and deposition of new matrix. A number of growth factors, including the fibroblast growth factors (FGF) and vascular endothelial growth factors (VEGF) are integrally involved in the angiogenic response in ischemic conditions and in certain pathological states. The availability of these factors has led to studies, which have demonstrated a therapeutic benefit in various animal models of the treatment of acute and chronic myocardial ischemia. In particular, basic fibroblast growth factor is an attractive candidate as an agent for therapeutic angiogenesis. Besides treating heart disease, these growth factors and stem cells are useful in the treatment of diseases of many other organs of the body.

Currently, stem cells are used to treat damage of an organ, including damage caused by ischemia. However, these treatments fail to prevent and/or lesson the organ damage to begin with. There is a need in the art for a treatment method using stem cells that prevents and/or lessons the damage of the organ by focusing on upstream causes, including ischemia, so that the damage may not even occur.

SUMMARY OF THE INVENTION

The invention provides methods for treating patients using cord blood and or tissue derived stem cells to prevent, lesson, or delay ischemia or prevent, lesson, or delay the complications of ischemia included but not limited to stroke, MI, aging, diabetes and/or critical limb ischemia. Currently, the state of the art is to use stem cells to treat the damage of an organ, including damage caused by ischemia. With the present invention, ischemia itself is treated in order to provide prevention, so that the damage to the organs may not even occur while avoiding or mitigating further damage. Without being bound by theory, it is believed that by improving blood flow and preventing ischemia the patient may not age so quickly, so the subject method also has applications for use as an anti-aging protocol.

The invention provides a method to prevent, lesson, or delay ischemia, or prevent, lessen, or delay the progression of arteriosclerosis, or prevent, lesson, or delay the complications of ischemia by administering an effective amount of stem cells derived from cord blood and or tissue. Preferably therapy is initiated, via invasive or noninvasive methods, when there is at least 20% occlusion of the external carotid arteries, internal carotid arteries, cerebral arteries, coronary arteries. Since peripheral artery disease can increase the risk of MI by sixfold, therapy will be initiated when the ankle-brachial index is less than or equal to 0.85. Therapy may also be initiated when there is evidence of decreased perfusion when the BP is less than 97/65, or the heart rate is less than 49, when the ejection fraction is less than 49%, or cardiac output is less than 3.7. Patients will be followed at 1 month, 3 months, 6 months, or yearly intervals. If there is greater than 2% worsening of the original occlusion, Ankle-brachial index decreases by at least 0.02, BP does not increase, heart rate does not increase, ejection fraction does not increase, and or cardiac output does not increase, then an additional effective amount of stem cells derived from cord blood and or tissue can be administered. The same process can be repeated as needed unless there is contraindication to therapy. Therapy can be administered sooner than one month intervals if the patient is experiencing worsening symptoms of ischemia, evidence of progression of arteriosclerosis, evidence of complications of ischemia, syncope or presyncope.

Without being bound by theory, it is hypothesized that since the cord blood and or tissue derived stem cells are growth factor factories they have a similar effect to that of stem cells combined with growth factors or growth factors alone. Advantageously, a continuous extended release of FGF from the factory takes place instead of multiple doses of administered FGF, which may be cumbersome, and not even feasible depending on the delivery system.

One aspect the invention provides a method for treating aging by delivering stem cells derived from cord blood AND or tissue for anti-aging, comprising the steps of: a) selecting a patient with at least 20% occlusion of at least one of external carotid arteries, internal carotid arteries, cerebral arteries, or coronary arteries; b) administering at least one dose consisting of an effective amount of stem cells collected from umbilical cord blood and/or tissue, wherein administration is intravenous (IV), intra thecal, intra-arterial, via catheter into the organ, via Myostar catheter into the heart, intracoronary, intrapericardial, or by direct injection into the organ; c) monitoring the effectiveness of administration by a monitoring means at selected time periods and determining if there is 2% or more occlusion and administering a second dose of said stems cells derived from cord blood and or tissue by a method that is at least invasive as that utilized in b; d) repeating steps b) and c) until there is at least one or clinical indication of: (i) prevention, lessening or delay of ischemia, (ii) prevention, lessening or delay in progression of arteriosclerosis, (iii) prevention, lessening or delay of complications of ischemia, or (iv) until there is contraindication to continued treatment; e) repeating b) and c) at a time x earlier than the selected time periods if there are complications of ischemia; and f) if necessary, repeating steps b) and c) until there is improvement of the complication of ischemia or until there is contraindication to continued treatment.

In a further aspect of the invention, there is provided a method for treating aging by delivering stem cells derived from cord blood or tissue for anti-aging, comprising the steps of: a) selecting a patient with decreased perfusion as evidenced by one or more selected perfusion indicators; b) administering at least one dose consisting of an effective amount of stem cells collected from cord blood or tissue, wherein administration is intravenous (IV), intra thecal, intra-arterial, via catheter into the organ, via Myostar catheter into the heart, intracoronary, intrapericardial, or by direct injection into the organ; and c) repeating b) until the one or more selected perfusion indicators shows an improvement y or until there is contraindication to continued treatment, wherein repeat dose of stem cells, if administered, is administered by a method that is at least as invasive as the method utilized for the administration of the dose of stem cells in b).

In a still further aspect, of the invention provides a method for treating aging by delivering stem cells derived from cord blood or tissue for anti-aging, comprising the steps of: a) selecting a patient with at least 15% occlusion of either peripheral arteries by invasive or noninvasive methods; b) administering at least one dose consisting of an effective amount of stem cells derived from cord blood or tissue, wherein administration is by IV, intra-arterial, via a catheter into the organ, or by direct injection into the organ; c) monitoring monthly, quarterly, semiannually, or yearly by the invasive or noninvasive methods above and determining if the occlusion worsens by 2% or more, or the ABI is worse by at least 0.02, giving a second dose of stem cells derived from cord blood or tissue, and if administered, administered by a method at lease as invasive as the previous dose of stem cells; d) if necessary repeating b) and c) to continue to: (i) prevent, lessen or delay ischemia; (ii) prevent, lessen or delay the progression of arteriosclerosis, (iii) prevent or lessen or delay the complications of ischemia, or (iv) until there is contraindication to continued treatment; e) repeat b) and c) earlier than 1 month if there are complications of ischemia, comprising one or more of worsening or severe claudication, critical limb ischemia, risk of amputation, leg muscle death; and f) if necessary repeat steps b) and c) until there is improvement of claudication, critical limb ischemia, risk of amputation, and or leg muscle death or until there is contraindication to continued treatment.

In yet a further aspect of the invention, there is contemplated a method for preventing or treating ischemia for preventing or managing disease by delivering stem cells derived from cord blood or tissue, consisting of: (a) selecting a patient suffering disease caused in at least some part by ischemia or at risk for ischemia; (b) administering at least one dose consisting of an effective amount of stem cells collected from umbilical cord blood and/or tissue, wherein administration is intravenous (IV), intra thecal, intra-arterial, via catheter into the organ, via Myostar catheter into the heart, intracoronary, intrapericardial, or by direct injection into the organ; (c) monitoring the effectiveness of administration at selected time periods and determining if there is an improved clinical indication, and administering a second dose of said stems cells derived from cord blood and or tissue by a method that is at least invasive as that utilized in (b); and (d) repeating steps (b) and (c) until the clinical indication shows improvement or until there is contraindication to continued treatment.

BRIEF DESCRIPTION OF THE DRAWINGS

The invention will be more fully understood and further advantages will become apparent when reference is had to the following detailed description of the preferred embodiments of the invention and the accompanying drawings, wherein like reference numerals denote similar elements throughout the several views, and in which.

DETAILED DESCRIPTION OF THE INVENTION

Figure 1:
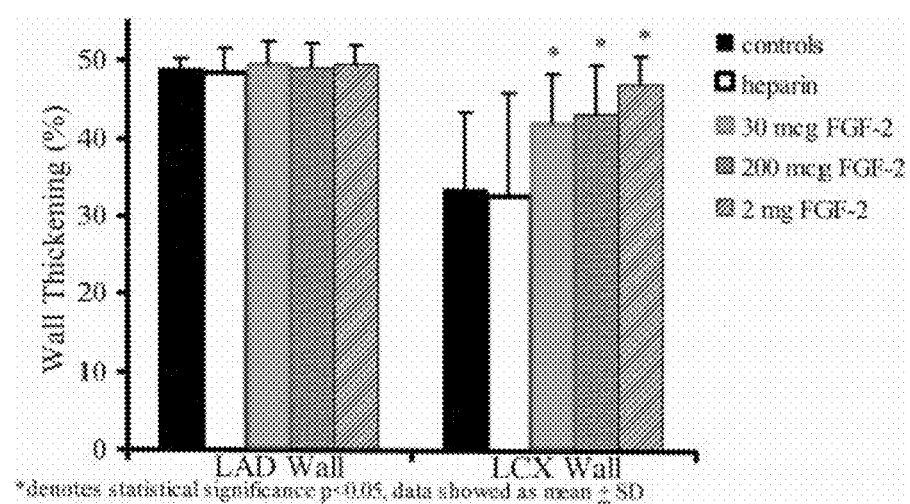
FIG. 1 is an illustration of the results of measured regional wall thickening in the LAD (normal) and LCX (collateral-dependent) distribution.

Generally stated, the invention relates to the treatment of patients suffering from acute or chronic diseases of the organs by treating upstream ischemia using at least one of the following: stem cells derived from cord blood and/or tissue. FGF-1 and FGF-2; and at least one of the following: VEGF, VEGFA, VEGFB, PLGF, VEGF121, VEGF145, VEGF165; VEGF189, VEGF206 and mixtures, thereof. Using cord blood and or tissue derived stem cells the subject invention provides methods to prevent, lesson, or delay ischemia or complications of ischemia, included but not limited to stroke, MI, and critical limb ischemia. The method also has applications in preventing, reversing and/or slowing down aging of skin tissue and organs through treatment of upstream ischemia caused by aging.

One aspect the invention provides a method for treating aging by delivering stem cells derived from cord blood or tissue for anti-aging, comprising the steps of: a) selecting a patient with at least 20% occlusion of at least one of external carotid arteries, internal carotid arteries, cerebral arteries, or coronary arteries; b) administering at least one dose consisting of an effective amount of stem cells collected from umbilical cord blood and/or tissue, wherein administration is intravenous (IV), intra thecal, intra-arterial, via catheter into the organ, via Myostar catheter into the heart, intracoronary, intrapericardial, or by direct injection into the organ; c) monitoring the effectiveness of administration by a monitoring means at selected time periods and determining if there is 2% or more occlusion and administering a second dose of said stems cells derived from cord blood and or tissue by a method that is at least invasive as that utilized in b; d) repeating steps b) and c) until there is at least one or clinical indication of: (i) prevention, lessen or delay ischemia, (ii) prevention, lessen or delay in progression of arteriosclerosis, (iii) prevention, lessen or delay of complications of ischemia, or (iv) until there is contraindication to continued treatment; e) repeating b) and c) at a time x earlier than the selected time periods if there are complications of ischemia; and f) if necessary, repeating steps b) and c) until there is improvement of the complication of ischemia or until there is contraindication to continued treatment. The 20% occlusion and monitoring means may be determined by one or more invasive method, such as angiogram, or non-invasive methods. Noninvasive methods are preferably at least one of carotid ultrasound, transcranial ultrasound, MRA, Spectscan, functional neuroimaging, and nuclear stress testing. The selected time period for determining the effectiveness of administration is monthly, quarterly, semi-annually, or yearly. Time x is preferably less than the selected time period, preferably at least less than 1 month, if there the complications of ischemia are present. Complications of ischemia comprise TIA's, stroke, unstable angina, and MI, and wherein, if necessary, repeating steps b) and c) until there is improvement of the TIA, stroke, unstable angina, MI or until there is contraindication to continued treatment.

In a further aspect of the invention, there is provided a method for treating aging by delivering stem cells derived from cord blood or tissue for anti-aging, comprising the steps of: a) selecting a patient with decreased perfusion as evidenced by one or more selected perfusion indicators; b) administering at least one dose consisting of an effective amount of stem cells collected from cord blood or tissue, wherein administration is intravenous (IV), intra thecal, intra-arterial, via catheter into the organ, via Myostar catheter into the heart, intracoronary, intrapericardial, or by direct injection into the organ; and c) repeating b) until the one or more selected perfusion indicators shows an improvement y or until there is contraindication to continued treatment, wherein repeat dose of stem cells, if administered, is administered by a method that is at least as invasive as the method utilized for the administration of the dose of stem cells in b). Preferably, the selected perfusion indicators for determining decreased perfusion, determined after adequate fluid intake, comprise at least one of: i) blood pressure less than 97/65; ii) pulse less than 49; iii) ejection fraction less than 49%; or iv) cardiac output less than 3.7. The improvement y of the one or more selected perfusion indicators preferably comprises at least one of: i) BP is at least 119/79; ii) pulse is at least 59; iii) ejection fraction is at least 54%; or iv) cardiac output is at least 3.9.

In a still further aspect, of the invention provides a method for treating aging by delivering stem cells derived from cord blood or tissue for anti-aging, comprising the steps of: a) selecting a patient with at least 15% occlusion of either peripheral arteries by invasive or noninvasive methods; b) administering at least one dose consisting of an effective amount of stem cells derived from cord blood or tissue, wherein administration is by IV, intra-arterial, via a catheter into the organ, or by direct injection into the organ; c) monitoring monthly, quarterly, semiannually, or yearly by the invasive or noninvasive methods above and determining if the occlusion worsens by 2% or more, or the ABI is worse by at least 0.02, giving a second dose of stem cells derived from cord blood or tissue, and if administered, administered by a method at lease as invasive as the previous dose of stem cells; d) if necessary repeating b) and c) to continue to: (i) prevent, lessen or delay ischemia; (ii) prevent, lessen or delay the progression of arteriosclerosis, (iii) prevent or lessen or delay the complications of ischemia, or (iv) until there is contraindication to continued treatment; e) repeat b) and c) earlier than 1 month if there are complications of ischemia, comprising one or more of worsening or severe claudication, critical limb ischemia, risk of amputation, leg muscle death; and f) if necessary repeat steps b) and c) until there is improvement of claudication, critical limb ischemia, risk of amputation, and or leg muscle death or until there is contraindication to continued treatment. Preferably, the at least 15% occlusion of either peripheral arteries is determined by one or more invasive methods comprising angiogram, and/or by one or more noninvasive methods comprising Ankle-brachial index < or = to 0.85, or estimated by Doppler studies.

In yet a further aspect of the invention, there is contemplated a method for preventing or treating ischemia for preventing or managing disease by delivering stem cells derived from cord blood and or tissue, consisting of: a) selecting a patient suffering disease caused in at least some part by ischemia or at risk of ischemia; b) administering at least one dose consisting of an effective amount of stem cells collected from umbilical cord blood and/or tissue, wherein administration is intravenous (IV), intra thecal, intra-arterial, via catheter into the organ, via Myostar catheter into the heart, intracoronary, intrapericardial, or by direct injection into the organ; c) monitoring the effectiveness of administration at selected time periods and determining if there is an improved clinical indication, and administering a second dose of said stems cells derived from cord blood and or tissue by a method that is at least invasive as that utilized in b; and d) repeating steps b) and c) until the clinical indication shows improvement or until there is contraindication to continued treatment. Preferably the disease is diabetes Type I or II, and monitoring comprises monitoring of Hemoglobin A1c at the selected time period of three (3) months during stem cell therapy, wherein improved clinical indication is presented when Hemoglobin A1c is lowered, thereby lowering further risk of diabetic complications. Alternatively, the disease is at least one of Ischemia, arteriosclerosis, complications of ischemia, decreased perfusion, or complications of diabetes including Ischemia, arteriosclerosis, complications of ischemia, autonomic neuropathy, and risk when Hemoglobin A1c is elevated.

The invention provides a method to prevent, lesson, or delay ischemia, or prevent, lessen, or delay the progression of arteriosclerosis, or prevent, lesson, or delay the complications of ischemia by administering an effective amount of stem cells derived from cord blood and or tissue. Preferably therapy is initiated, via invasive or noninvasive methods, when there is at least 20% occlusion of the external carotid arteries, internal carotid arteries, cerebral arteries, coronary arteries. Since peripheral artery disease can increase the risk of MI by sixfold, therapy will be initiated when the ankle-brachial index is less than or equal to 0.85.

Therapy may also be initiated when there is evidence of decreased perfusion when the BP is less than 97/65, or the heart rate is less than 49, when the ejection fraction is less than 49%, or cardiac output is less than 3.7. Patients will be followed at 1 month, 3 months, 6 months, or yearly intervals. If there is greater than 2% worsening of the original occlusion, Ankle-brachial index decreases by at least 0.02, BP does not increase, heart rate does not increase, ejection fraction does not increase and or cardiac output does not increase, then an additional effective amount of stem cells derived from cord blood and or tissue can be administered. The same process can be repeated as needed unless there is contraindication to therapy. Therapy can be administered sooner than one month intervals if the patient is experiencing worsening symptoms of ischemia, evidence of progression of arteriosclerosis, evidence of complications of ischemia, syncope or presyncope.

Since the cord blood and or tissue derived stem cells are growth factor factories they have a similar effect to that of stem cells combined with growth factors or growth factors alone. A continuous extended release of FGF advantageously results from the factory takes place instead of multiple doses of administered FGF, which may be cumbersome, and not even feasible depending on the delivery system. Combination of FGF and VEGF provides a synergistic effect in the treatment of the diseased organ.

Gene therapy may also be used for pretreating the diseased organs, wherein the gene therapy is AD5 (FGF4) or VEGF 165 plasmid DNA. After pretreating the diseased organ, the patient is treated with cell therapy. The cell therapy includes one or more of the following: hematopoetic stem cells, endothelial stem cells, hepatic stem cells, neuronal stem cells, muscle stem cells, cardiac stem cells, adult stem cells, embryonic stem cells, epidermal stem cells, adipose stem cells, mesenchymel stem cells, cord blood stem cells, umbilical cord stem cells, placental stem cells, dental stem cells, epithelial stem cells, stem cells obtained from a zygote, stem cells obtained from a blastocys, stem cells from any organ, stem cells from any tissue, neurons, oligodentrocytes, astrocytes, cells from any organ, cells from any tissue and combinations thereof. The diseased organ may include but is not limited to the brain, spinal cord, pancreas, liver, kidney, muscle, heart and upper and lower gastrointestinal tracts. The invention relates to a multi-tiered approach to the treatment of acute or chronic diseases of the organs. Initially the patient is treated with growth factors including at least one of: FGF-1 and FGF-2; and at least one of: VEGF, VEGFA, VEGFB, PLGF, VEGF121, VEGF145, VEGF165; VEGF189, VEGF206, and mixtures thereof. The factors utilized with gene therapy include AD5(FGF4) and/or VEGF165 plasmid DNA. The growth factors prime the organ that has been damaged by ischemia or other disease. The extent of improvement is monitored by ultrasound, MRI, CAT scan, cardiac echo, EEG, EKG, EMG or blood tests.

In another embodiment of the present invention, the patient is treated with growth factors including at least one of: FGF-1, FGF-2, VEGF, VEGFA, VEGFB, PLGF, VEGF121, VEGF145, VEGF165; VEGF189, VEGF206, and mixtures thereof. The growth factors prime the organ that has been damaged by ischemia or other means. As in the previous embodiment, following administration of at least one dose of an effective amount of a first therapeutic growth factor protein formulation, administrating at least one dose of an effective amount of adult stem cells or other cell therapy is performed. The extent of improvement is monitored by ultrasound, MRI, CAT scan, cardiac echo, EEG, EKG, EMG or blood tests.

Of the various treatment modalities currently in use or under investigation for the delivery of therapeutically effective doses of various growth factor proteins, a wide range of levels of invasiveness are involved. Intravenous administration is among the least invasive, but questions remain as to the ultimate delivery of the proteins to physiological sites at therapeutically effective levels. Next most invasive is intracoronary infusion through catheters. The insertion and manipulation of catheters has seen increasingly widespread use in the treatment of the symptoms of heart disease and a number of other clinical conditions. However, for most, if not all, cardiac patients, there is a very low level of toleration of such catheterization procedures, so that the possibility of repeated deliver of growth factor proteins is extremely limited.

Next on the relative scale of invasiveness is intrapericardial injection of growth factors. Although requiring more substantive surgical procedures, this technique can be utilized in conjunction with other surgical procedures such as coronary artery bypass surgery and would, thus, not constitute an additional traumatic burden on the patent. Alternatively, relatively minor incisions can be made in the chest wall to permit direct interpericardial delivery. Again, due to the invasive nature of the procedures utilized in this manner of delivery, the possibility of repeated administration via this route is very low.

The most invasive delivery method is direct injection of FGF and related proteins. This, of course, requires surgery to achieve access to the delivery site. As such, this approach is mostly feasible when used in conjunction with surgical intervention for other purposes, such CABG. Again, the major drawback here is that it is very impractical to repeatedly deliver the therapeutic proteins via this delivery method.

The growth factors can be administered via intravenous injection, intracoronary infusion, intrathecal injection, intra-arterial injection, retrograde venous injection to the organ, direct injection into the organ, injection through the lymphatic system and injection through the biliary ducts.

To assess the efficacy of VEGF and/or FGF, you could follow the extent of improvement of the diseased organ by monitoring with ultrasound, MRI, CAT scan, cardiac echo, EEG, EKG, EMG or blood tests.

Alternative delivery methods for the treatment of acute and chronic diseases of the organs should also be considered. FGF and/or VEGF could be administered by intrathecal, intra-arterial to the organ, retrograde venous injection to the organ, or through the lymphatic system, or through the biliary ducts. When injected directly into the organ, slow release forms of FGF or VEGF should be considered.

To prime the diseased organ for the implantation of adult stem cells or other cell therapy, the least invasive method can be attempted depending on the clinical status of the patient. If the least invasive approaches are not successful in achieving clinical improvement, then alternate delivery systems should be explored. As clinically indicated the FGF and/or VEGF could be given by direct injection into the diseased organ.

Of the various treatment modalities currently in use or under investigation for the delivery of therapeutically effective doses of various growth factor proteins, a wide range of levels of invasiveness are involved. Obviously, intravenous administration is among the least invasive, but questions remain as to the ultimate delivery of the proteins to physiological sites at therapeutically effective levels. Next most invasive is intracoronary infusion through catheters. The insertion and manipulation of catheters has seen increasingly widespread use in the treatment of the symptoms of heart disease and a number of other clinical conditions. However, for most, if not all, patients, there is a very low level of toleration of such catheterization procedures, so that the possibility of repeated deliver of growth factor proteins is extremely limited.

Next on the relative scale of invasiveness is intra-arterial injection of growth factors to the organ. Relatively minor incisions can be made to permit direct intra-arterial delivery. Again, due to the invasive nature of the procedures utilized in this manner of delivery, the realistic possibility of repeated administration via this route is very low.

At the most invasive end of the spectrum is direct injection of FGF and related proteins. This, of course, requires surgery to achieve access to the delivery site. As such, this approach is most feasible only when used in conjunction with surgical intervention for other purposes. Again, the major drawback here is that there is very little practical opportunity for repeated delivery of the therapeutic protein.

Recognizing the large scope of therapies potentially available in the treatment of acute and chronic diseases of the organs, it is therefore an aspect of the present invention to provide a systematic, multi-tiered therapeutic approach to the administration of FGF, VEGF or gene therapy followed by cell therapy. This approach must, of necessity, recognize the relative invasiveness of different treatment modalities, and the likelihood of repeated recourse to such treatment procedures.

This pretreatment by growth factors conditions the organ to allow optimal implantation of cells during the cell therapy phase of the invention and improves trafficking of stem cells to ischemic or damaged areas. Stem cells or other cell therapy need active perfusion to survive and grow. The growth factors protect the stem cells from reperfusion injury. In addition, FGF and/or VEGF can improve the trafficking of the stem cells to the diseased or ischemic or damaged organ. The growth factors would increase blood flow optimizing the implantation and differentiation of the stem cells. See, U.S. Pat. No. 4,296,100. The growth factors may also prevent ischemic damage to the stem cells or other cell therapy. See, U.S. Pat. No. 4,296,100.

Ventricular remodeling is in part determined by neovascularization and increased apoptosis, especially in the border zone of the infarction. Circulating stem cells have regenerative capacity and can repair some of the damaged organ following a disease. Growth factor pretreatment followed by cell therapy enhances organ tissue regeneration and restores organ function.

One of the mechanisms by which adult stem cell exert a positive effect is that they become growth factor "factories". The growth factors they produce improve blood flow (see U.S. Pat. No. 4,296,100), decrease inflammation, and decrease aptosis. Because of this effect, adult stem cells would be beneficial in the treatment of acute and chronic ischemia of any organ, including but not limited to the heart, brain, and pancreas.

Autism is considered to be the result of neural hypoperfusion. By improving blood flow adult stem cells may prove to be a beneficial treatment for this disorder. The stem cells could be administered in a variety of methods including, but not limited to intravenously, intra-arterially, and direct injection to the brain. These stem cells could be administered by themselves or be preceded by, and/or in conjunction with growth factors.

Cell therapy can be given alone or can follow growth factor treatment. The length of time between growth factor treatment and cell therapy depends on several factors. These include the degree of angiogenesis with growth factor pretreatment, the extent of organ damage, and the prognosis for the patient. The time period may be as short as 1 minute and as long as 2 months. One skilled in the art would be able to determine the length of time between growth factor pretreatment and cell therapy without undue experimentation depending upon the clinical status of the patient.

Cell therapy can involve the use of bone marrow stem cells, skeletal myoblasts, mesenchymal stem cells, or peripheral blood stem cells (PBSC). Human bone marrow stem cells have been shown to traffic to nonhematopoietic organs where they can differentiate into cells. Human adult mesenchymal stem cells are accessible from the bone marrow and peripheral blood and can differentiate into endothelial cells and cardiomyocytes. There is growing evidence that adult bone marrow cells can function to repair disease by repopulating damaged organs.

One type of cell for use in cell therapy is the peripheral blood stem cell (PB SC). These are cells that are isolated from the peripheral blood from either the patient or from an HLA-matched donor. PBSC can be collected without the use of general anesthesia, and the procedure is usually performed on an outpatient basis with little or no discomfort during, or after, the collection. Most importantly, more stem cells can often be collected from the peripheral blood than from the bone marrow. The PBSC may be isolated from the peripheral blood through apheresis. The PBSC may be further purified by fluorescence-activated cell sorting or density gradient centrifugation.

Stem cells may also be collected successfully and derived from umbilical cord blood and tissue. In addition, mesenchymal stem cells may be derived from cord blood, cord tissue, dental tissue, placental tissue, bone marrow, and fat.

The route of delivery that is selected for the stem cells is crucial in that it helps to determine whether or not repair of the damaged organ will occur. A high stem cell concentration near the damaged area increases the chances that sufficient stem cell localization and differentiation occurs in order to repair the organ. In many cases this involves the targeted and regional administration of stem cells.

In one embodiment, the route of delivery of the stem cells or other cell therapy is intracoronary administration. The stem cells or other cell therapy may also be administered by injection through intrathecal, intra-arterial, retrograde venous injection to the organ, or direct injection into the organ or injection through the lymphatic system or injection through the biliary ducts.

The stem cells or other cell therapy may also be delivered to the border area of the infarct. As one skilled in the art would be aware, the infarcted area is visible grossly, allowing the specific placement of stem cells or other cell therapy to be possible.

In another embodiment, the route of delivery is by intravenous injection. This route of delivery has the advantage of being the easiest to administer. The disadvantage of this route of delivery is that many of the stem cells or other cell therapy will spend a considerable time in the circulation system before the stem cells or other cell therapies reach the infarct-related organ.

Additional routs of delivery for the stem cells includes intravenous administration, intracoronary administration, intrathecal administration, intra-arterial administration, and retrograde venous injection to the organ, direct injection into the organ, injection through the lymphatic system and injection through the biliary ducts.

Organ regeneration following growth factor treatment and cell therapy is monitored by ultrasound, MRI, CAT scan, cardiac echo, EEG, EKG, EMG or blood tests. If it is determined that insufficient cell differentiation was occurring, then cell therapy is modified to increase delivery of stem cells or other cell therapy to the affected area. Thus, if it is determined by ultrasound, MRI, CAT scan, cardiac echo, EEG, EKG, EMG or blood tests that there is insufficient cell regeneration, then the number of stem cells or other cell therapy is increased or a more invasive route for stem cell delivery is used.

A variety of stem cells have been used to treat the complications of ischemia, such as stroke, Myocardial Infarction (MI), and critical limb ischemia (See examples 8 and 11 below). For example, TCA Cellular used mesenchymal stem cells derived from bone marrow to treat critical limb ischemia. Osiris used the same type of cell to treat MI. Stem cells derived from cord blood/tissues are growth factor factories, including for the production of FGF. FGF has been used to treat coronary ischemia. (See Examples 1-7 below). FGF has also been used to treat MI (See for example, U.S. Pat. No. 4,296,100).

Contrary to these teachings, through the subject method it has been found that instead of waiting for complications of ischemia, stem cells derived from cord blood and/or tissue can be used to prevent or lessen or delay ischemia itself. Thereby preventing, lessening or delaying the progression of arteriosclerosis, and preventing, lessening or delaying the complications of ischemia. Also, it has been found through use of the subject method, stem cells derived from cord blood and/or tissue can be used to lessen the effects of decreased perfusion of the organs from decreased blood pressure (BP), heart rate, cardiac output, and/or ejection fraction. Preferably, treatment through the subject method is initiated with stem cells derived from cord blood and/or tissue when the BP is less than 97/65, the heart rate is less than 49, the ejection fraction is less than 49% and or the cardiac output is less than 3.7.

Treatment may be initiated by invasive (angiogram) and/or noninvasive testing, such as carotid ultrasound, MRA, transcranial ultrasound, functional neuroimaging, Spectcan, ankle brachial index, nuclear stress test. Preferably, there is approximately less than 20% perfusion by BP and heart rate, approximately less than 10% perfusion by ejecton fraction and cardiac output and/or greater than 20% occlusion of the carotid arteries (internal or external), cerebral arteries, coronary arteries, and/or peripheral arteries. Patients are preferably monitored monthly, quarterly, biannually, or yearly.

If there is evidence of a 2% worsening of occlusion or an ABI decreases by at least 0.02, a repeat treatment can be initiated. A repeat treatment can be initiated sooner if there is evidence of worsening symptoms of ischemia, complications of ischemia, syncope, and or presycope. Hemoglobin A1c can be monitored and therapy can be initiated to prevent or lessen or delay the diabetic complications of ischemia.

The following examples are presented to provide a more complete understanding of the invention. The specific techniques, conditions, materials, proportions and reported data set forth to illustrate the principles and practice of the invention are exemplary and should not be construed as limiting the scope of the invention.

EXAMPLE 1

Intracoronary Injection of FGF-2 in the Treatment of Severe Ischemic Heart Disease: A Maximally Tolerated Dose Study Patient selection. The study was conducted at two centers, the Beth Israel Deaconess Medical Center (Boston, Mass.) and Emory University Hospital (Atlanta, Ga.), and patients were enrolled between December 1997 and July 1998. The study was approved by the Institutional Review Boards at both hospitals. The inclusion criteria selected for patients with advanced CAD with inducible ischemia and who were considered to be suboptimal candidates for either PTCA or CABG. Patients were excluded from the study if they had any of the following criteria: uncompensated congestive heart failure or an ejection fraction<20%; a myocardial infarction within three months; new onset of angina or unstable angina within three weeks; PTCA, CABG, stroke or transient ischemic attack within six months; uncontrolled hemodynamically significant arrhythmias; critical valvular disease; restrictive or hypertrophic cardiomyopathy; arteriovenous malformations; proliferative retinopathy, retinal vein occlusion, or macular edema; renal insufficiency (creatinine clearance<80 ml/min by 24-h urine collection); vasculitis or chronic immunosuppressive therapy; or any malignancy within the past 10 years (except for curatively treated nonmelanoma skin cancer). Patients with diabetes mellitus were eligible if they had no proliferative retinopathy or severe nonproliferative retinopathy, and no microalbuminuria.

Patient population. Fifty-two patients met all eligibility criteria and received a single IC infusion of rFGF-2. The mean age was 60.8±10.1 years (range 41 to 80) and 2 of 52 patients were women. Six patients (11%) had diabetes mellitus and 31 patients (60%) had elevated cholesterol (serum cholesterol>200 mg/dl). Forty-three patients (83%) had a history of at least one prior CABG. The mean ejection fraction (evaluated by MR imaging) was 51.4±12.0% (range 20% to 73%). Sixty-nine percent of patients had NYHA class II or III symptoms of congestive heart failure.

Study design. This was an open-label interpatient dose escalation study. The initial dose of 0.33 g/kg was escalated over eight sequential groups to 48 g/kg IC. At least four patients were studied at each dose. If no patient experienced dose-limiting toxicity as defined by the protocol within six days, the dose was escalated; if one patient experienced dose-limiting toxicity, an additional four patients were studied at that dose. The MTD was defined as the dose tolerated by 9 of 10 patients.

Study procedures. After providing informed consent and meeting all eligibility criteria, patients underwent baseline evaluations that included a complete medical history and physical examination, an ophthalmologic examination with fundus photography read by a core laboratory using the Early Treatment Diabetic Retinopathy score (ETDRS), an exercise tolerance test (ETT), a Seattle Angina Questionnaire (SAQ), and nuclear and MRI cardiac scans. Measurement of initial health status allowed the use of change in scores, thus adjusting for differences in baseline health. Self-administration was used instead of telephone interview to minimize data collection bias.

On day 1, patients underwent right and left heart catheterization and coronary angiography. If the coronary anatomy was not amenable to PTCA or CABG, recombinant FGF-2 (rFGF-2, Chiron Corporation, Emeryville, Calif.) was infused with a Baxter pump through diagnostic catheters into two major conduits of myocardial blood supply over 20 min (10 min in each vessel) with continuous monitoring of systemic blood pressure and right atrial and pulmonary capillary wedge pressures, and cardiac output. In occasional patients, the entire dose was infused into a single vessel that was believed to be the major source of blood supply. Prior to initiation of rFGF-2 infusion, normal saline was administered intravenously (IV), if required, to ensure mean pulmonary capillary wedge pressure>12 mm Hg. Heparin (40 U/kg) was administered IV more than 10 min before rFGF-2. The volume of infusion varied with dose and the patient's weight, ranging from 10 ml at lower does to 40 ml at higher doses.

The right heart (Swan-Ganz) catheter was left in place for 7 h following drug infusion to monitor filling pressures and cardiac output. Patients were monitored with full-disclosure telemetry for 24 h following rFGF-2 administration. Patients were discharged 24 h after study drug infusion and clinical follow-up visits were performed at days 6, 15, 29, 57, 180 and 360. Quality of life was assessed using the Seattle Angina Questionnaire at baseline and days 57 and 180. ETT's were obtained at days 29, 57 and 180. Exercise stressed nuclear perfusion scans (rest thallium/stress $^{99m}$Tc-sestamibi) and resting cardiac magnetic resonance scans were performed at days 29, 57 and 180.

Preliminary Efficacy of RFGF-2 Therapy. Although the small sample size and the absence of a control group preclude any definitive conclusions regarding efficacy, several findings suggest potential clinical benefits of intracoronary rFGF-2 administration. In particular, quality of life, as assessed by the SAQ, improved in treated patients at day 57 compared with baseline, and this improvement was sustained for six months. The magnitude of improvements in the five SAQ scales was similar to that seen following PTCA and CABG in patients with ischemic heart disease. There was also a significant improvement in exercise capacity, as measured by exercise treadmill testing, seen at days 57 and 180. Of note, there was minimal improvement at day 29. The late occurrence of improvement in exercise testing is in keeping with the assumed time course of coronary angiogenesis. However, the absence of a dose response tempers the preliminary efficacy seen in this study.

In addition, to these subjective measures of clinical status, resting MR imaging was performed to assess left ventricular function and myocardial perfusion. Using this approach, we detected no difference in overall left ventricular ejection fraction at any time during the study. However, there was a significant improvement in systolic thickening of the target wall at day 29, which was maintained at six months, and was paralleled by a significant reduction in the size of the ischemic myocardium as assessed by blood arrival imaging. Although cardiac MR imaging is considered the "gold standard" for evaluation of left ventricular function, its application to clinical trials in coronary disease is very limited. Similarly, despite recent advances in MR-based perfusion assessment of the myocardium, there has been no substantial clinical experience with this imaging modality. Prior animal studies have documented improvement in MR-assessed parameters of left ventricular function in the setting of angiogenic growth factor therapy. In addition, the newly developed variation of MR perfusion imaging that relies on generation of space-time maps proved capable of detecting changes in coronary perfusion in a pig ameroid model and proved capable of detecting improved regional myocardial perfusion in patients treated with epicardially administered sustained release FGF-2.

A fundamental question pertaining to IC delivery is how a drug with a relatively short plasma half-life can promote a relatively long-term process such as new collateral formation. One possible explanation is that first-pass extraction at the desired site of action is the primary determinant of FGF-2 biological effect. Although such extraction certainly occurs, animal studies demonstrated that <1% of $^{125}$I-FGF-2 administered using the intracoronary route is deposited in the myocardium at 1 h and much less remains at 24 h. Although there is enhanced first-pass FGF-2 uptake in ischemic compared with normal myocardium, presumably due to increased expression of cellular heparin sulfates and FGF receptor-1, myocardial levels fall to very low levels at 24 h in both normal and ischemic regions of the heart. One speculative explanation is that this transient accumulation of FGF-2 in the ischemic myocardium sets in motion a self-amplifying cascade that includes the influx and endothelial adhesion of monocytes/macrophages and stimulation of expression of VEGF and other angiogenic cytokines, which may lead to prolonged and sustained action.

Safety Assessment. The safety of intracoronary rFGF-2 was assessed through clinical observations, electrocardiography, hemodynamic monitoring, hematologic and serum chemistry profiles, development of anti-rFGF-2 antibodies, detailed ophthalmological exams with fundus photography and assessment of renal function by determination of creatinine clearance and proteinuria using 24-h urine collection. Dose-limiting toxicity was predefined as a persistent (>10 min) drop in systolic blood pressure by >50 mm Hg, change in heart rate to >120/min or to <50/min, new clinically significant arrhythmia, new ischemic symptoms or ECG changes, new congestive heart failure, deterioration in renal function or any other serious adverse events.

Clinical follow-up and safety assessment. Clinical follow-up of at least six months was obtained on all patients. A total of 30 serious adverse events were reported in 22 patients. There was no apparent relationship between increasing dose of rFGF-2 and serious adverse events.

Four patients died. Two deaths were sudden and occurred 22 days (0.65 g/kg dose, EF 30%) and 114 days (48 g/kg dose, EF 22%) after rFGF-2 infusion. One death was due to complications of cardiac transplantation and one death was due to complications of large-cell lymphoma. Both instances of sudden death occurred in patients with reduced left ventricular function (22% and 30%). Although sudden death may be part of the natural history of their disease, potential partial revascularization in these patients may have induced ventricular tachyarrhythmias. The diagnosis of large-cell non-Hodgkin's lymphoma 10 days after rFGF-2 infusion most likely reflected the presence of disease that antedated IC rFGF-2 administration. Nevertheless, it is possible that rFGF-2 may have exacerbated the lymphoma course.

One patient (2 g/kg) died 72 days after rFGF-2 infusion from complications of cardiac transplantation after sustaining several myocardial infarctions beginning four days after drug infusion. One patient with preexisting lymphadenopathy (6 g/kg) died at 62 days from septic complications of large-cell lymphoma, which was diagnosed at 10 days after dosing. In retrospect, the lymphoma most likely predated rFGF-2 infusion. One additional patient was diagnosed with metastatic adenocarcinoma to the liver at day 431.

Four patients had non-Q-wave myocardial infarctions at days 5 (2 g/kg dose group), 68 (6 g/kg), 132 (0.33 g/kg) and 146 (48 g/kg). Four patients had revascularization procedures (CABC and aortic value replacement in one patient at day 68 [6 g/kg] and PTCA in three patients at day 100 (0.33 g/kg), 290 [24 g/kg], and 223 [48 g/kg]). One patient developed atrial fibrillation at day 37. The most commonly reported (>10% of patients) adverse events were asthenia (19%), hypotension (15%), dyspnea (13%), insomnia (13%), angina (12%) and palpitations (12%). Of these asthenia, hypotension, insomnia, and dyspnea were more common at higher doses. No patients withdrew from the study because of adverse events. Transient leukocytosis was observed in half the patients at.gtoreq.24 g/kg. Fluctuations in renal function occurred but were transient and not dose related. Proteinuria (>250 mg/24 h) occurred in four patients (7.8%). Ophthalmological exams with fundus photography at baseline and day 57 were available for 45 patients; seven patients lacked wither baseline or 57-day assessments. Forty patients (89%) showed no change from baseline, two patients improved by two ETDRS grades and three patients worsened by two grades (0.65, 2.0 and 36.0 g/kg groups).

Safety and Tolerability of RFGF-2 Administration. The ability to administer fairly high doses of rFGF-2 (up to 36 g/kg IC) without significant hemodynamic effects is somewhat surprising given prior reports of severe FGF-2-induced hypotension and the known capacity of this cytokine to stimulate NO release and induce arteriolar vasodilation. Hypotension was dose-related and dose limiting, but was rapidly correctable by IV fluids. This finding is in sharp contrast to clinical experience with another NO-releasing growth factor, VeGF-$A_{165}$, where profound hypotension limits systemic administration. This difference in part may be attributable to careful hemodynamic monitoring in these patients and a requirement for adequate pressure (>12 mm Hg) before initiation of rFGF-2 infusion.

Preclinical studies as well as limited clinical experience to date suggested that renal insufficiency due to membranous nephropathy accompanied by proteinuria may be the most significant long-term side effect of FGF-2 administration. In this small trial, only four instances of proteinuria were observed. In should be noted, however, that all patients studied had normal renal function at baseline.

Additional serious side effects included the occurrence of non-Q-wave myocardial infarction in four patients, raising the possibility that FGF-2 may have promoted growth, or destabilization of coronary plaque owing to its broad-spectrum mitogenicity and chemotactic activity. The latter possibility may be particularly relevant given the ability of FGFs to induce angiogenesis in vasa vasorum and the association between plaque angiogenesis and its growth and stability. Although these concerns are certainly worrisome, in the absence of a control group casual relationships cannot be confirmed or discounted.

Statistical methods. Data are pooled for all dose groups. Baseline characteristics and acute hemodynamic parameters are expressed as mean. +− standard deviation. Efficacy variables were analyzed using a linear mixed effects model with an unstructured covariance assumption for the repeated measurements, fit using the restricted maximum likelihood method. Model-based estimates of the means. +− standard errors (SEM) are presented. An overall F-test for equality across all time points was conducted first. If this initial test was statistically significant, pairwise t tests to compare baseline with each on-study time point were performed at the nominal a-level. All reported p-values are two-sided, and a p-value<0.05 was considered statistically significant.

Magnetic resonance (MR) imaging. Magnetic resonance (MR) imaging was performed at baseline and days 29, 57 and 180 in the body coil of a 1.5 T whole-body Siemens Vision or Philips NT system. Functional imaging was performed during breath-hold using shared-center FLASH or multishot echoplanar imaging in each of the three mutually perpendicular standard views, producing 16-24 sequential image frames each, collected over approximately 12 heartbeats to measure regional wall systolic thickening. MR blood arrival imaging was assessed as previously described. A series of four inversion recovery images was obtained with the inversion time (TI) adjusted to minimize signal intensity from myocardium. Using the best TI for nulling myocardial signal, a series of concurrent parallel images were acquired in diastole during breathhold, at baseline and after the bolus injection of contrast media (0.05 mmol/kg gadodiamide). Measurement of the timing of half-maximum signal arriving in the different parts of the myocardium demonstrated the existence of several distinct regions, including normal myocardium and areas exhibiting delayed contrast arrival (ischemic zones). For each scan, a pace-time map demonstrating distribution of contrast signal density over the left ventricular wall as a function of time was created. The extent of the territory demonstrating delayed arrival of contrast, defined as >1-s delay of contrast density reaching its 50% maximum value reflecting the most severely hypoperfused part of the myocardium, was then calculated and expressed ads percent of the total left ventricular myocardial area. MR analysis was performed by a core lab blinded to rFGF-2 dose assignment and to study sequence.

Quality of life assessment. There were significant improvements in all five scales of the Seattle Angina Questionnaire at days 57 and 180, as compared with baseline. Angina frequency score increased (denoting improvement) from 39.8±3.8 at baseline to 68.8±4.0 (p<0.001) at day 57 and 64.7±4.5 at day 180 (p<0.001), overall p<0.001. Exertional capacity score increased from 49.2±2.8 at baseline to 64.5±3.1 at day 57 (p<0.001) and 73.0±3.8 at day 180 (p<0.001), overall p<0.001.

Exercise treadmill testing. A subset of patients with matching baseline and follow-up exercise treadmill protocols was selected for analysis. Among this group, the mean exercise time improved from 510±24 s at baseline (n=35) to 561±26 s at day 29 (n=28; p=0.023), 609±26 s at day 57 (n=31; p<0.001), and 633±24 sat day 180 (n=23; p<0.001).

Left ventricular function assessment. Magnetic resonance imaging was performed in 51 patients at baseline and was repeated at days 29 (n=47), 57 (n=45) and 180 (n=31) to assess resting left ventricular ejection fraction, regional wall motion, and myocardial contrast arrival. There was a small improvement in overall left ventricular ejection fraction over the course of the study (baseline 51.4±1.7%, day 29: 54.2±1.7% [p=0.02], day 57: 55.2±1.9% {p=0.003}, day 180: 57.2±1.7% [p<0.001], overall p=0.002). The hypoperfused target area was selected for resting regional left ventricular wall motion analysis. Systolic thickening of this area (target wall) and normal wall were measured using a semiautomated quantification algorithm of short-axis MR images. Resting normal wall systolic thickening was 46.1±1.6% at baseline and did not change significantly throughout the study duration (p=0.16). Resting target wall thickening was significantly lower than normal wall thickening at baseline (34.0±1.7% vs. 46.1±1.6%, p<0.001). Target wall thickening significantly improved at days 29, 57, and 180 as compared to baseline [baseline: 34±1.7%, day 29: 38.7.+−.1.9% (p=0.006), day 57: 41.4±1.9% (p<0.001), and day 180: 42.0±2.3% (p<0.001), overall p=0.001].

Myocardial perfusion assessment. Myocardial perfusion was assessed using MR imaging. The mean size of the delayed contrast arrival zone was 15.4±0.8% of the left ventricle at baseline and was like the global left ventricular extent of ischemia determined by nuclear perfusion imaging (17.3±1.8%). The size of the myocardial area demonstrating delayed contrast arrival was significantly reduced from baseline (15.4±0.8%) at day 29 (9.0.+−.0.6%, p<0.001), day 57 (5.6±0.7%, p<0.001) and day 180 (4.9±0.8%, p<0.001), overall p<0.001. There was no correlation between the dose and the various efficacy parameters studied.

EXAMPLE 2

Safety and Efficacy of a Single Intrapericardial Injection of FGF-2 In a Porcine Model of Chronic Myocardial Ischemia Chronic Myocardial Ischemia Model. Yorkshire pigs of either sex weighing 15 to 18 kg (5-6 weeks old) were anesthetized with intramuscular (IM) ketamine (10 mg/kg) and halothane by inhalation. A right popliteal cut-down was performed and a 4 French arterial catheter was inserted for blood sampling and pressure monitoring. Left thoracotomy was performed through the 4th intercostal space. The pericardium was opened, and an ameroid constrictor of 2.5 mm id. (matched to the diameter of the artery) was placed around the left circumflex coronary artery (LCX). The pericardium was closed using 6-0 Prolene suture, (J&J Ethicon, Cincinnati, Ohio) and the chest was closed. A single dose of IV cefazolin (70 mg/kg) was given, and IM narcotic analgesics were administered as needed. Animals then were allowed to recover for 3 weeks (time sufficient for ameroid closure) before growth factor delivery. The treatment of animals was based on the National Institutes of Health guidelines, and the protocol was approved by the Institutional Animal Care and Utilization Committee of the Beth Israel Deaconess Medical Center.

Growth Factor Delivery. Three weeks after ameroid placement, animals were anesthetized with IM ketamine (10 mg/kg) and isoflurane by inhalation. A right femoral cut-down was performed and an 8 French arterial sheath was inserted for blood sampling, pressure monitoring, and left heart catheterization. Coronary angiography was then performed in multiple views using a 7 French JR4 diagnostic catheter (Cordis, Miami, Fla.) to confirm LCX occlusion and to assess the extent of collateral circulation in the LCX distribution ("collateral index"). After LCX occlusion was documented, percutaneous subxyphoid pericardial access was undertaken. With the animals in the supine position, the epigastric area was prepped and draped. An epidural introducer needle (Tuohy-17) was advanced gently under fluoroscopic guidance with a continuous positive pressure of 20 to 30 mm Hg. Entry into the pericardial space was confirmed by the injection of 1 ml of diluted contrast. A soft floppy-tipped guidewire was then advanced into the pericardial space and the needle was exchanged for a 4 French infusion catheter.

The animals were randomized to one of five treatment groups:
1. Control: intrapericardial saline (n=10).
2. Heparin: intrapericardial heparin (3 mg, n=9).
3. FGF-2 30 μg: intrapericardial FGF-2 (30 μg)+3 mg of heparin (n=10).
4. FGF-2 200 μg: intrapericardial FGF-2 (200 μg)+3 mg of heparin (n=10).
5. FGF-2 2 mg: intrapericardial FGF-2 (2 mg)+3 mg of heparin (n=10).

The infusate was diluted to 10 ml with saline and infused over 5 min with continuous electrocardiographic and pressure monitoring. The catheter was withdrawn, and a set of colored microspheres (blue) was injected into the left atrium to obtain baseline (pretreatment) myocardial blood flow. Finally, a magnetic resonance study was carried out to obtain quantitative measures of global and regional left ventricular function [ejection fraction (EF) and radial wall motion] and assessment of perfusion using myocardial contrast density mapping. The animals then were allowed to recover for 4 weeks.

Final Study. Four weeks after intrapericardial agent administration, all animals underwent final evaluation. Pigs were anesthetized with IM ketamine (10 mg/kg) and isoflurane by inhalation. A left femoral cut-down was performed and an 8 French arterial sheath was inserted for blood sampling, pressure monitoring, and left heart catheterization. Coronary angiography was performed again in multiple views. A second magnetic resonance study was carried out for global and regional left ventricular function and myocardial perfusion.

Myocardial blood flow was determined using colored microspheres at rest (yellow) and after maximal coronary vasodilation with IV adenosine (white). Animals then were euthanized under anesthesia and the heart was obtained for additional analysis. In addition, a detailed macroscopic and histologic postmortem examination was carried out on three animals in each group.

A total of 56 animals survived ameroid placement around the LCX coronary artery with resultant total LCX occlusion at 3 weeks. Seven animals died after being randomized to a treatment group. Six of these seven animals died within 72 h of intrapericardial agent delivery. Of the seven animal's deaths, two animals died of hypoxemia (one control animal and one FGF-2-30 μg animal) due to failure of mechanical ventilation before growth factor delivery, four animals died during MRI (three animals died before growth factor delivery and one after pericardial access and delivery, with two animals randomized to the 200 μg FGF-2 group and two animals in the control group), and one animal died of unknown cause 26 days after growth factor delivery (heparin group). The remaining 49 animals were randomized to each of five treatment groups with 10 animals in each of the FGF-2 and saline control groups and 9 animals in the heparin group. There were no significant hemodynamic effects of intrapericardial FGF-2 administration at any dose; no changes in blood pressure, heart rate, or left atrial pressure were observed with drug administration.

Angiographic Analysis. Coronary angiography was performed in multiple views (right anterior oblique, anteroposterior, and left anterior oblique views for the left coronary artery; right anterior oblique and left anterior oblique for the right coronary artery). Evaluation of angiographic collateral density was performed by two independent angiographers blinded to treatment assignment. Differences in interpretations were resolved by a third angiographer. The collateral index was assessed for left-to-left and right-to-left collaterals using a 4-point scale (0, no visible collateral vessels; 1, faint filling of side branches of the main epicardial vessel without filling the main vessel; 2, partial filling of the main epicardial vessel; and 3, complete filling of the main vessel).

Coronary Angiography Baseline right and left coronary angiography was available on all 49 animals and final angiography was available on 47 animals. Left-to-left collaterals and right-to-left collaterals were measured (collateral index). The extent of left-to-left collaterals pre- (3 weeks after ameroid placement) and post-treatment (7 weeks after ameroid placement) in all groups shows a significant improvement over baseline in the collateral index of all three FGF-2 treatment groups (30 μg, 200 mμg and 2 mg) with no significant improvement noted in control or heparin-treated animals. Only animals in the FGF-2 2 mg group displayed a trend toward improvement in right-to-left collateral index (collateral index increased by 0.67±0.87, P=0.06).

Myocardial Blood Flow. Colored microspheres (15±0.1 μm diameter; Triton Technology Inc., San Diego, Calif.) were used to determine coronary blood flow before treatment initiation (blue) and at the time of final study (yellow and white). For determination of coronary flow at 3 and 7 weeks after ameroid placement, an angiographic JR4 catheter was advanced into the left ventricle and manipulated to engage the left atrium outflow by slow counterclockwise rotation of the catheter; catheter position was verified by contrast injection into the left atrium. In addition, mean left atrial pressure was recorded. A set of microspheres ($6 \times 10^6$) was diluted in 10 ml of saline and injected into the left atrium over 30 s. Reference blood samples were withdrawn by using a syringe pump at a constant rate of 5 ml/min through the femoral artery. At the time of final study, coronary flow was measured at rest and after maximal vasodilation (achieved with the injection of IV adenosine, 1.25 mg/kg). After study completion, the heart was excised and regional myocardial blood flow was determined. The heart was excised and a 1-cm midtransverse slice was sectioned and cut into eight segments. The tissue samples and the reference blood samples were digested in an 8 M KOH/2% Tween 80 solution and microspheres were collected using a vacuum filter. Dyes from microspheres were extracted using dimethyl formamide. Samples were then analyzed in a spectrophotometer (HP 8452 A; Hewlett Packard, Palo Alto, Calif.).

Regional blood flow was calculated from optical absorbance (AU) measurements corrected by tissue weight as follows:

Flow to sample (ml/min/g)=(AU/sample) (reference withdrawal rate)/wt./(AU/reference sample)

To evaluate further the angiogenic potential of intrapericardial FGF-2 in chronic myocardial ischemia, regional myocardial blood flow was measured at different time points using colored microspheres. Three weeks after implantation of ameroid occluders, at the time of intrapericardial drug delivery, resting myocardial blood flow in the LCX territory was similar in all treatment groups [baseline coronary flow (ml/min/g): 1.00±0.31 in controls and 0.97±0.23 in heparin-treated animals versus 0.92±0.08 in the 30 μg FGF-2 group, 0.99±0.15 in the 200 μg FGF-2 group, and 1.10±0.14 in the 2 mg FGF-2 group, P=0.94] and was significantly lower than flow in the LAD territory (LCX flow: 1.00±0.35 ml/min/g versus LAD flow: 1.43±0.43 ml/min/g, P<0.0001). Four weeks after intrapericardial drug delivery, LCX flow was significantly higher in FGF-2-treated animals than in controls and heparin-treated animals (ANOVA P=0.002). At the time of the final study, coronary flow (ml/min/g) was 1.05±0.21 in controls (P=0.7 compared with baseline) and 1.09±.0.13 in the heparin group (P=0.19 compared with baseline and P=0.6 compared with controls) versus 1.31±.0.12 in the 30 μμg FGF-2 group (P=0.0001 compared with baseline and P=0.004 compared with controls), 1.25±0.15 in the 200 μg FGF-2 group (P=0.002 compared with baseline and P=0.03 compared with controls), and 1.32±0.16 in the 2 mg FGF-2 group (P=0.004 compared with baseline and P=0.005 compared with controls).

MRI. MRI was performed on all animals at the time of treatment initiation and at the time of final study. MRI was carried out in the body coil of a 1.5 Tesla whole body Siemens Vision system (Iselin, N.J.) as previously described. The following measurements were performed:
a. Determination of resting left ventricular EF (%).
b. Analysis of regional wall motion using percentage of wall thickening.
c. Determination of the extent of coronary perfusion in the LCX collateral-dependent territory compared with normal myocardium by measuring gadodiamide-enhanced signal intensity in different parts of the left ventricular wall and generating a space-time map of myocardial perfusion). The space-time maps allow the measurement of the extent of the ischemic zone.

MRI was available on 44 animals (8 in the control group; 9 in the heparin group; and 9 in each of the 30 μg, 200 μg, and 2 mg FGF-2 groups). In five animals, MRI was not performed due to temporary technical problems with the MRI system at the time of the final study. The porcine ameroid occlusion model is associated with the development of small areas of left ventricular myocardial necrosis in most animals.

Global Left Ventricular Function. To assess the functional significance of FGF-2-mediated improvement in myocardial blood flow, MRI was used to assess global and regional left ventricular function in all study animals. There were no significant differences in global left ventricular function among the five groups (EF was 44.1±6.4% in controls and 44.2±6.8% in heparin-treated animals versus 47.07±2.68 in the 30 μg FGF-2 group, 45.52±3.41 in the 200 mg FGF-2 group, and 47.98±3.14 in the 2 mg FGF-2 group; ANOVA, P=0.35).

Figure 2:
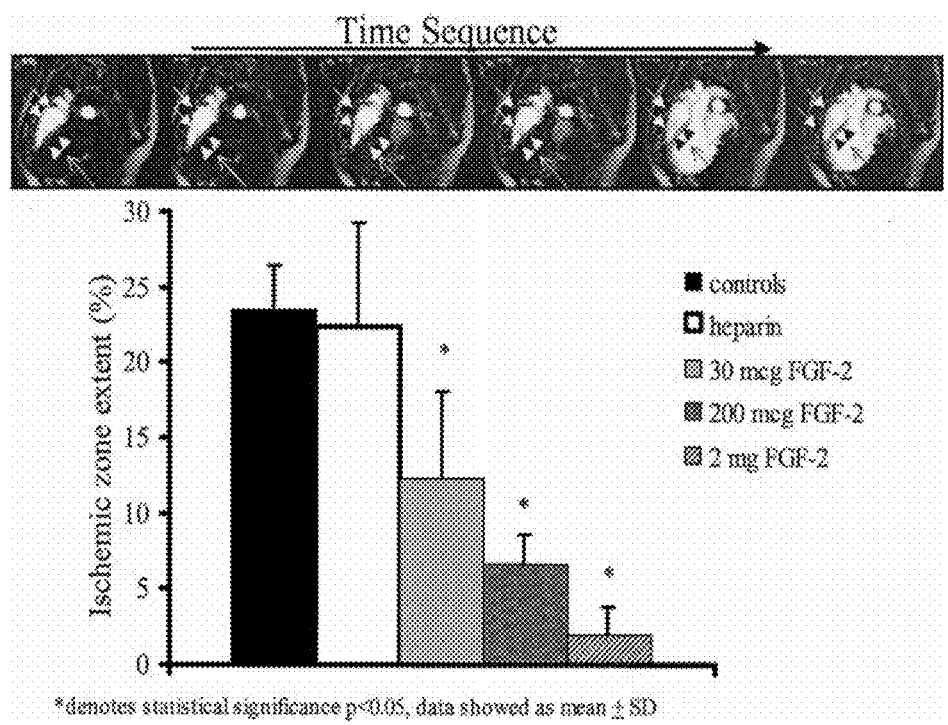
FIG. 2 is an illustration of, at top, MRI perfusion images of the left ventricle and, at bottom, the ischemic zone extent in all groups of test animals.

Regional Left Ventricular Function. Measurement of regional wall thickening in the LAD (normal territory) and LCX (ischemic) territories was used to assess regional left ventricular function (FIG. 2). LAD (normal) wall thickening was similar in all groups (ANOVA, P=0.86). FGF-2-treated animals had improved regional wall thickening in the LCX (ischemic) territory compared with controls and heparin-treated animals [FIG. 2; LCX wall thickening (%): controls, 33.58±9.91; heparin, 32.64±13.45 (P=0.87 compared with controls); FGF-2 30 μg, 42.12±6.43 (P=0.05 compared with controls); FGF-2 200 μg, 43.23±6.41 (P=0.03 compared with controls); and FGF-2 2 mg, 47.14±3.64 (P=0.002 compared with controls); ANOVA, P=0.003]. Linear regression (assuming heparin results in no significant FGF-2 release) revealed a dose-dependent improvement in LCX wall thickening in the FGF-2-treated animals (y=37.6±0.005x, P=0.007)

Figure 3:
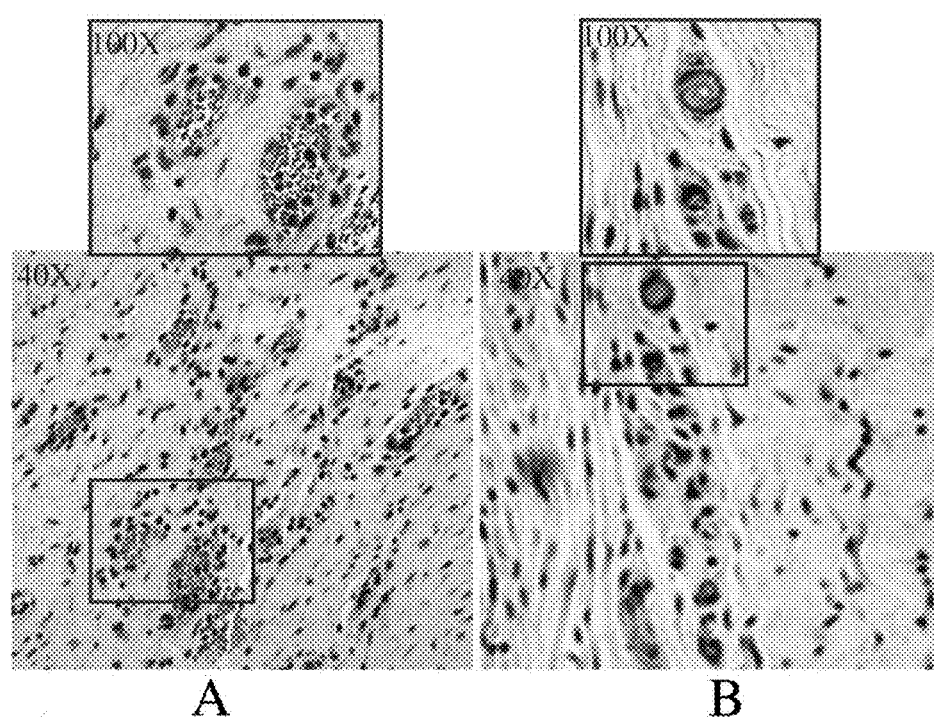
FIG. 3 is an illustration of histopathological sections from the LCX distribution demonstrating an increased number of capillaries in all treatment groups.

Myocardial Perfusion. First-pass inversion-recovery turboFLASH MRI was used to generate a space-time map of myocardial perfusion (FIG. 3 top). Three distinct zones are observed that are characterized by either prompt signal appearance, failure of the signal to increase in intensity (infarction), or delayed signal appearance (delayed contrast arrival or ischemic zone). On the basis of contrast density data, a two-dimensional map of contrast intensity versus time was generated and was used to measure the size of the myocardial segments showing impaired (delayed) contrast arrival. FIG. 3 (bottom) depicts the extent of the ischemic zone of contrast in the five groups. FGF-2 induced a dose-dependent reduction in the extent of the ischemic zone, indicating achievement of better myocardial perfusion in the FGF-2 treatment groups [FIG. 3 bottom; ischemic zone (% of left ventricle): controls, 23.54±2.84; heparin, 22.41±6.85 (P=0.66 compared with controls); FGF-2 30 μg, 12.27±5.82 (P=0.0001 compared with controls); FGF-2 200 μg, 6.63±1.97 (P<0.0001 compared with controls); and FGF-2 2 mg, 2.02±1.83 (P<0.0001 compared with controls); ANOVA, P<0.0001; linear regression y=16.7-0.008x, P<0.00011].

Histopathologic Analysis and Toxicology. Complete autopsies were performed on 15 animals (3 animals in each group). Tissues obtained from the liver, lung, kidney, spleen, eye, bone marrow, and stomach were formalin-fixed and paraffin-embedded. Sections (5 um) were obtained from all tissue samples, stained with hematoxylin/eosin, and examined microscopically. In addition, tissue samples were obtained from pericardium, epicardial coronary artery, and myocardium in the left anterior descending coronary artery (LAD) distribution (normal) and LCX distribution (ischemic). Sections were stained with hematoxylin/eosin as well as by the Verhoeff-Van Gieson method for collagen and elastin. Complete serum chemistry and hematology studies were performed at 3 and 7 weeks in all animals.

There were no treatment-related macroscopic or microscopic findings in any of the organs examined. One animal had a single kidney present. There was focal to diffuse minimal thickening of the pericardium in all FGF-2 treatment groups, which was due to a slight increase in connective tissue (fibrosis). There were minimal to mild chronic inflammatory cell infiltrates accompanied by focal or multifocal mineralization in all FGF-2 treatment groups. Increased vascularity was noted in the pericardium of two of three animals examined in the 200 μg FGF-2 group and one of three animals examined in the 2 mg FGF-2 group, but was not observed in the control, heparin, or 30 μg FGF-2 groups (FIG. 4B). In addition, the LAD and LCX in these animals were examined and they showed no evidence of intimal hyperplasia.

Finally, there was an increase in vascularity of the epicardium and myocardium in all animals from the 30 μg, 200 μg, and 2 mg FGF-2 groups, but not in controls or heparin-treated animals. Sections from the LCX but not the LAD distribution in all FGF-2 treatment groups showed an increase in the number of capillaries. Many of these small blood vessels were lined by endothelial cells that had large hyperchromatic nuclei, suggestive of new vascular in-growth (FIG. 4A). FGF-2 treatment did not result in any significant abnormalities in serum chemistries, hematology, and coagulation studies.

EXAMPLE 3

Nonmitogenic Effects of Administration of FGF-2 in Acute Myocardial Ischemia and Reperfusion in a Murine Model To determine whether nonmitogenic effects of FGF-2 could be beneficial to the heart during acute myocardial ischemia and reperfusion, FGF-2 was administered in a murine model of myocardial stunning. The advantages of this mouse model are well-defined markers of ischemia-reperfusion injury, including ischemic contracture, alteration in calcium homeostasis, and prolonged ventricular dysfunction, occurring within a time window too short to activate the mitogenic properties of FGF-2. Transgenic mouse hearts deficient in the expression of the inducible isoform of NOS (NOS2-/-) were used to further investigate the coupling of FGF-2 and NO during acute myocardial ischemia and reperfusion.

Stunning. Myocardial stunning is the phenomenon whereby an ischemic insult interferes with normal cardiac function, cellular processes, and ultrastructure for prolonged periods. Numerous mechanisms of myocardial stunning have been proposed, the most probable of which include generation of oxygen-derived free radicals, metabolic impairment, and calcium overload. Recently, a number of pharmacological agents and physiological manipulations have been shown to induce early or late ischemic preconditioning, a state characterized by reduced susceptibility to postischemic decline in myocardial function. In particular, FGF-2 has been demonstrated to improve myocardial function in the setting of acute myocardial ischemia both in vivo and in isolated rat heart studies. The well-known angiogenic effects of FGF-2, however, occur too gradually to be relevant in such settings. The purpose of this study, therefore, was to study the potential role of NO release in FGF-2-mediated cardioprotection and to define the NOS isoform responsible for FGF-2-induced NO release.

Fifteen minutes of global ischemia followed by twenty minutes of reperfusion resulted in prolonged ventricular dysfunction characterized by reduced levels of LVP generation as well as significant decreases in $dP/dt_{max}$ and $dP/dt_{min}$. Pretreatment with rFGF-2 significantly improved the extent of recovery of LVP compared with control (untreated) hearts (83±5 vs. 61±6%) and equally significant preservation of $dP/dt_{max}$ and $dP/dt_{min}$ (86±3 vs. 65±6% and 85±5 vs. 60±5%, respectively. Stunning in hearts perfused with either NOS inhibitor by itself was not different from that in control hearts. Functional recovery of LVP in untreated control hearts (61±6%) was not significantly different from that in hearts perfused with either L-NAME alone (59.+-.9%) or L-NIL alone (57±6%). Depression of $dP/dt_{max}$ and $dP/dt_{min}$ (65±6 and 60.±5%, respectively) in untreated hearts was similar to that in hearts perfused with L-NAME alone (60±9 and 55±8%, respectively) and hearts perfused with L-NIL alone (57±9 and 67±4%, respectively).

Unlike initial pretreatment with rFGF-2, addition of the growth factor to the coronary perfusate after the onset of ischemia, immediately before reperfusion, did not improve LV function 20 min after reperfusion (LVP 60±4%, dP/dtmax 62.+-.4%, and $dP/dt_{min}$ 58±4%, all P=NS vs. control). As in the case of acute ischemic changes, pretreatment with either L-NAME or L-NIL led to a complete inhibition of rFGF-2 effects (FIGS. 2 and 3).

Isolated Heart Preparation. Hearts were excised from adult C57/BL6 mice of either sex that had been anesthetized and heparinized (500 U/100 g body wt). The aorta was slipped over a 20-auge blunt-tipped stainless steel needle through which oxygenated (95% $O_2$-5% $CO_2$) Krebs-enseleit (KH) buffer (in mM: 118.0 NaCl, 4.7 KCl, 1.2 $KH_2PO_4$, 1.5 $CaCl_2$, 1.2 $MgCl_2$, 23.0 $NaHCO_3$, 10.0 dextrose, and 0.3 EDTA, pH 7.4) was pumped at a rate of $^{-3}$ml/mm. An intraventricular balloon catheter system specially designed for the mouse heart was passed through the mitral annulus into the left ventricle, and the distal end of the balloon catheter was connected to a Statham P23b (Gould, Cleveland, Ohio) transducer to record intraventricular pressure, Left ventricular (LV) pressure recordings were analyzed with regard to LV developed pressure (LVP), LV end-diastolic pressure, peak rate of pressure development ($dP/dt_{max}$), time to 90% pressure decline, and peak rate of pressure decline ($dP/dt_{min}$).

Ischemia and reperfusion. The hearts were subjected to no-flow ischemia for 15 min. The organ bath was evacuated of its oxygenated solution and refilled with nitrogen-saturated perfusate. Pacing was maintained during ischemia. LV pressure was monitored throughout ischemia and reperfusion. All hearts ceased to contract within 3 min. The time for LVP to fall to 10% of baseline ($T_{LVP10}$) was measured to quantify differences in LV function during early ischemia. Mean ischemic $Ca_i^2+$ was calculated as the mean $Ca_i^2+$ recorded from the 2nd through the 14th minute of ischemia. Contracture was defined as an abrupt and sustained rise in intraventricular pressure above 4 mmHg. Contracture time was measured as the time from the onset of ischemia to the onset of contracture. At the end of 15 mm of ischemia, the nitrogen-saturated bath was replaced by the original bath maintained at 30° C. Flow was recommenced. Mean $Ca_i^2+$ during early reflow was calculated as the mean of the peaks of $Ca_i^2+$ recorded during the 1st minute of reperfusion. After 20 min of reperfusion, $Ca_i^2+$ and functional parameters were again measured.

Drugs. Recombinant bovine FGF-2 (rFGF-2) was obtained from Chiron (Sunnyvale, Calif.). NG-nitro-L-arginine methyl ester (L-NAME), an inhibitor of NOS, was obtained from RBI (Natick, Mass.). $L-N_6$ -(1-iminoethyl) lysine (L-NIL), a selective inhibitor of NOS2, was obtained from Sigma (St. Louis, Mo.). All studies were conducted at 30.degree. C., and hearts were paced at 6 Hz to minimize consumption of aequorin. After a 15-min equilibrium period, baseline conditions were recorded. Subsequently, hearts were divided into the following perfusion groups: perfusion with KH for 40 min (control, n=10), perfusion with KH for 20 min followed by perfusion with KH plus 1 μg/ml rFGF-2 for 20 min (rFGF-2, n=10), perfusion with KH plus 400 μM L-NAME for 20 min followed by perfusion with KH plus 400 μM L-NAME plus 1 μg/ml rFGF-2 for 20 min (L-NAME+rFGF-2, n=6), and perfusion with KH plus 400 μM L-NIL for 20 min followed by perfusion with KH plus 400 μM L-NIL plus 1 μg/ml rFGF-2 for 20 min (L-NIL+rFGF-2, n=5). To test the effect of perfusion with the NOS inhibitors in the absence of rFGF-2, the following two additional perfusion groups were studied: perfusion with KH for 20 min followed by perfusion with KH plus 400 μM L-NAME for 20 min (L-NAME, n=5), and perfusion with KH for 20 min followed by perfusion with KH plus 400 μM L-NIL for 20 min (L-NIL, n=5).

Measurement of Intracellular $Ca^2+$ In hearts in which intracellular $Ca^2+$ ($Ca_i^2+$) was estimated, aequorin was injected into the apex of the heart. Briefly, after the perfusate was modified to contain 0.5 mM $CaCl_2$, 0.6 mM $MgCl_2$, and 20 mM dextrose, 1-3 μl of aequorin were injected with a glass micropipette into a localized region of 2 mm$^2$ at the apex of the heart. The heart was positioned in an organ bath such that the aequorin-loaded region was $^{-2}$ mm from the bottom of the bath. The $Ca^2+$ and $Mg^2+$ concentrations of the perfusate were increased to 2.5 mM $Ca^2+$ and 1.2 mM $Mg^2+$ in a stepwise fashion over a period of 40 min. The entire isolated heart preparation was positioned in a light-tight box for collection of the aequorin light signal. Aequorin luminescence was detected by a photomultiplier tube and recorded as anodal current. For estimation of $Ca_i^2+$, Triton X-100 was injected into the coronary perfusate to quickly permeabilize the myocardial cell membranes and expose the remaining active aequorin to saturating $Ca^2+$. This resulted in a burst of light, the integral of which approximated the maximum light ($L_{max}$) against which light signals of interest (L) provided the fractional luminescence ($L/L_{max}$). $L/L_{max}$ was referred to a calibration equation to estimate $Ca_i^2+$.

Myocardial Calcium Homeostasis. Changes in myocardial $Ca_i^2+$ are thought to play an important role in ischemia-induced myocardial dysfunction. Therefore, additional experiments were carried out to assess the effect of rFGF-2 administration on myocardial ionized calcium levels. Myocardial $Ca_i^2+$ measured at baseline was not different between NOS2+/+ and NOS2−/− hearts, and pretreatment with rFGF-2 had no effect on these levels. Interruption of coronary flow produced abrupt alterations in $Ca_i^2+$ in all hearts, with a gradual rise in diastolic and peak $Ca_i^2+$ as ischemia progressed. Mean ischemic $Ca_i^2+$, $Ca_i^2+$ averaged from the 2nd through the 14th minute of ischemia, was not affected by rFGF-2 pretreatment and was the same in NOS2+/+ and NOS2−/− hearts. Restoration of coronary flow was followed by a marked increase in myocardial $Ca_i^2+$. Neither the extent of this increase nor peak $Ca_i^2+$ levels was affected by rFGF-2 administration in NOS2+/+ or NOS2−/− hearts.

Measurement of NO Additional NOS2+/+ (n=5) and NOS2−/− hearts (n=5) were used to measure NO concentration in the coronary effluent using an amperometric sensor (ISO-NO, World Precision Instrument, Sarasota, Fla.). Briefly, after 20 min of perfusion with either vehicle or 1 μg/ml rFGF-2, the electrode was positioned in the effluent to measure the amount of NO released from the coronary sinus. Electrode calibration was performed before each experiment with NO generated from the reaction of S-nitroso-N-acetylpenicillamine (Sigma) with cupric sulfate (Sigma) and acidic solution.

Quantification of NOS Gene Expression To determine NOS2 and NOS3 mRNA levels in FGF-2-treated compared with control hearts, 30 cycles of RT-PCR were performed on equal amounts of total RNA from six control and six rFGF-2-treated hearts using primers corresponding to human NOS3 and NOS2 sequences. For NOS3, primers were as follows: 5' (sense), 5'-CAGTGTCCAACATGCT-GCTGGAAATTG-3' (bases 1,050-1,076) (SEQ ID NO: 1); antisense, 5'-TAAAGGTCTTCTTGGTGATGCC-3' (bases 1,511-1,535) (SEQ ID NO: 2). For NOS2, primers were as follows: 5' (sense), 5'-GCCTCGCTCTGGAAAGA-3' (bases 1,425-1,441) (SEQ ID NO: 3); antisense, 5'-TCCAT-GCAGACAACCTT-3' (bases 1,908-1,924) (SEQ ID NO: 4). Glyceraldehyde-3-phosphate dehydrogenase (GAPDH) mRNA was amplified from the same amount of RNA at the same time to correct for variation between different samples. The PCR products, separated on 1% agarose gels, were scanned and quantitated using Image-Quant software (Molecular Dynamics).

For Northern analysis of NOS1 and NOS3 mRNA levels in hearts of NOS2−/− and wild-type mice, total RNA was prepared from freshly excised hearts, subjected to electrophoresis on 1% paraformaldehyde-agarose gel, transferred to the GeneScreen Plus membrane (Dupont), and probed with random-primed mouse NOS1 and NOS3 cDNA probes. GAPDH cDNA probe was used to control for loading. Quantification was achieved using Image-Quant software.

Role of NOS2 The studies suggested that the NOS2 isoform was the primary NOS isoform responsible for FGF-2-induced preservation of myocardial function in this model. To further corroborate these results, the same studies were repeated in hearts from NOS2−/− mice using their NOS2+/+ littermates as controls. As in the case of previous studies, ischemia in both NOS2+/+ and NOS2−/− hearts was characterized by an abrupt fall in LV pressure, a gradual onset of ischemic contracture, and prolonged ventricular dysfunction throughout 20 min of reperfusion. rFGF-2 pretreatment prolonged $T_{LVP10}$, reduced the onset of contracture, and improved LV recovery throughout reperfusion.

However, in NOS2−/− hearts, rFGF-2 failed to provide any protective effects against global ischemia and stunning as measured by changes in LVP, dP/dt$_{max}$, and dP/dt$_{min}$ after 20 min of reperfusion.

Release of NO and FGF-2 Effects on NOS Gene Expression To directly demonstrate the role of rFGF-2-induced NO release, the concentration of NO in coronary effluent before and after rFGF-2 administration was measured. NO concentration increased significantly after perfusion with rFGF-2 compared with measurements after perfusion with vehicle (236±24 vs. 190±25 nM/g, P<0.05) in wild-type hearts. In contrast, perfusion with rFGF-2 did not increase NO concentration in NOS2−/− hearts compared with NO values measured after perfusion with vehicle (170±24 vs. 154±46 nM/g, P=NS). To assess whether rFGF-2 increased NO production by stimulating NOS enzyme or increasing its gene expression, we carried out RT-PCR analysis of NOS2 and NOS3 mRNA levels before and after 40 min of exposure to rFGF-2. No differences in either NOS2 or NOS3 levels were detected.

The "knockout" of the NOS2 gene may have affected expression of NOS1 or NOS3 genes in these mice. To evaluate this possibility, we performed Northern analysis of NOS1 and NOS3 gene expression in hearts from C57/BL6 NOS2+/+ and NOS2−/− mice. No significant changes in expression of either gene compared with that in control mice were detected.

Statistical Analysis Observations made before and after drug administration were compared using Student's two-tailed paired t-test. Observations made before and after the ischemia-reperfusion protocol within a group were compared using Student's two-tailed paired t-test. Between-group comparisons were made using analysis of variance. When an overall significance was observed, multiple comparisons were performed using the Bonferroni-modified t-test. A value of P<0.05 was considered significant. Data are expressed as means±SE.

Baseline Conditions and Effects of Ischemia Baseline parameters of cardiac function including myocardial $Ca_i^2+$ were similar at baseline in all groups and were not affected by administration of L-NAME, L-NIL (not shown), or rFGF-2. Interruption of coronary flow led to an abrupt fall in LV pressure in all hearts. This fall in LV pressure during early ischemia was significantly attenuated in hearts pretreated with rFGF-2 compared with control hearts. Pretreatment with rFGF-2 prolonged $T_{LVP10}$ (124±9 vs. 74±5 s, rFGF-2 vs. control, P<0.05) and significantly delayed the onset of contracture (893±7 vs. 819±36 s, rFGF-2 vs. control, P<0.01).

To explore the role of NO in mediation of this cardioprotective effect of FGF-2, L-NAME was used to inhibit all isoforms of NOS in the heart. Pretreatment with L-NAME completely blocked the cardioprotective effects of rFGF-2 during ischemia, significantly reducing $T_{LVP10}$ (79±2 vs. 124±9 s, L-NAME+rFGF-2 vs. rFGF-2, P<0.05) and accelerating the onset of ischemic contracture (674±24 vs. 893±7 s, L-NAME+rFGF-2 vs. rFGF-2, P+0.05). However, perfusion with L-NAME alone (in the absence of rFGF-2) did not affect either $T_{LVP10}$ [69.+−.3 vs. 74.+−.5 s, L-NAME vs. control, P+not significant (NS)] or the onset of ischemic contracture (820.+−.24 vs. 819.+−.36 s, L-NAME vs, control P+NS).

To further define the type of NOS enzyme involved in this FGF-2 response, a NOS2-selective inhibitor, L-NIL was used, Similarly to L-NAME, L-NIL fully inhibited the cardioprotective effects of rFGF-2, significantly reducing $T_{LVP10}$ (62.+−.3 vs. 124.+−.9 s, L-NIL+rFGF-2 vs. rFGF-2, P<0.05) and accelerating the onset of Ischemic contracture (652.+−.16 vs. 893.+−.7 s, L-NIL+rFGF-2 vs. rFGF-2, P<0.05). Similarly to perfusion with L-NAME, perfusion with L-NIL alone, in the absence of rFGF-2, did not affect either $T_{LVP10}$ (67.+−.6 vs. 74.+−.5 s, L-NIL vs. control, P+NS) or the onset of ischemic contracture (740.+−.39 vs. 819.+−.36 s, L-NIL vs. control, P+NS).

EXAMPLE 4

Efficacy of Intracoronary Versus Intravenous FGF-2 and a Porcine Model of Chronic Myocardial Ischemia A porcine ameroid model was chosen for preclinical testing of delivery strategies because of several unique aspects. First, the ameroid occluder results in consistent and gradual occlusion of the LCX, resulting in minimal myocardial necrosis, but reduced regional myocardial function, which is detectable with various noninvasive imaging modalities. Because an effect of estrogen on cardiac angiogenesis cannot be ruled out and synchronization of these studies with the menstrual cycle is logistically impossible, females were excluded from this study. In a similar model in dogs, daily intracoronary injections of FGF-2 also induced increased vascularity of ischemic myocardium. Although very encouraging, there are little data considering the efficacy of single intravascular administration of angiogenic growth factors.

MATERIALS AND METHODS Male Yorkshire pigs (n=57; Parsons, Hadley, Mass.) weighing 15 to 30 kg were used for this study. The chronic ischemia model consisted of three phases as previously described [4, 7]. In brief, for ameroid surgery and catheterization at 3 and 6 weeks, the animals were anesthetized with Ketamine 20 mg/kg IM and pentothal 10 mg/kg IV, intubated, mechanically ventilated, and further anesthetized with 1.5% to 2.5% isoflurane in room air. Postoperatively, all animals received antibiotics and analgesics for 48 hours. Animal care was performed according to the National Institutes of Health's Guidelines for the Care and Use of Laboratory Animals, and the protocol was approved by the Institutional Animal Care Committee.

A plastic ameroid (inner diameter, 2 to 2.5 mm; Research Instruments, Escondido, Calif.) was placed on the proximal left circumflex artery (LCX) or a major side branch, through a left lateral fourth intercostal thoracotomy. Three weeks (second phase, midstudy) later, right and left coronary catheterization was performed through a standard femoral cut-down after systemic anticoagulation with Heparin 100 U/kg. Intra-arterial pressure and electrocardiogram were continuously recorded. Selective left and right angiography (General Electric, Waukesha, Wis.; contrast: Renografin; Squibb Diagnostics, Princeton, N.J.) confirmed complete occlusion of the LCX and allowed assessment of baseline flow and the presence of collaterals in the LCX territory, according to the Rentrop scoring system from 0 to 3: 0=none; 1=filling of side branches of the LCX; 2=partial filling of the LCX main artery via collateral channels; 3=complete filling of the LCX. Angiographic analysis was blinded to treatment. For regional blood flow measurements, colored microspheres were injected into the left atrium (see below). Directly after this, function, perfusion, and collateral sensitive magnetic resonance imaging (MRI) was performed on all animals to quantify baseline regional cardiac function and perfusion before start of the treatment.

Pigs were then randomly assigned to one of the following treatments: 1) vehicle control; 2) 2 µg/kg rFGF-2 IV; 3) 6 µg/kg rFGF-2 IV; 4) 2 µg/kg rFGF-2 IC; 5) 6 µg/kg rFGF-2 IC. Five minutes before FGF-2 administrations, heparin (70 U/kg, IV) was given. Bovine recombinant FGF-2 (rFGF-2; Chiron Corporation, Emeryville, Calif.) was dissolved and diluted in vehicle consisting of 10 mmol/L sodium citrate, 10 mmol/L thioglycerol, 135 mmol/L sodium chloride, 100 mmol/L EDTA, pH 5.0. The intracoronary FGF-2 was equally divided and infused into the right coronary artery (RCA) and the proximal LCX using a 3F Cordis infusion catheter. Intravenous infusions were given through an ear vein. In short proximal LCX stumps, FGF-2 was delivered into the proximal part of the LAD. The vehicle control group consisted of animals that received intravenous vehicle (n=4) or intracoronary vehicle (n=4). Three weeks after therapy (third phase, final study), repeat selective angiograms were made and two sets of colored microspheres were injected into the left atrium, one before (rest) and one after injection of Adenosine 1.25 mg/kg IV (stress). Function and perfusion MRI was also repeated in all animals. Finally, animals were euthanized and the hearts were excised.

Fifty-seven animals received an ameroid constrictor and 13 animals died before initiation of treatment. Forty-four animals (control, n=10; FGF 2 µg/kg IV, n=9; FGF 6 µg/kg IV, n=9; FGF 2 µg/kg IC, n=8; and FGF 6 µg/kg IC, n=8) completed the entire study.

Regional blood flow For microspheres injection into the left atrium, a 7F JL4 catheter was retrogradely advanced across the aortic and mitral valve into the left atrium. The left atrial position of the catheter was confirmed by contrast injection and the presence of an atrial pressure waveform. At midstudy, and during the final study at rest and stress, $6 \times 10^6$ microspheres (Dye Trac; Triton Technologies, San Diego, Calif.) were injected according to a standard protocol Reference blood samples were drawn simultaneously. At the end of the study (final study), a mid papillary, 1-cm-thick cross section of left ventricle was taken and divided into eight radial segments. The segment in the LCX territory was further subdivided in an endocardial and epicardial piece. Tissue samples and reference blood samples were digested and the microspheres retrieved according to the manufacturer's protocol. The samples were analyzed with a spectrophotometer (SU 600; Beckman, Fullerton, Calif.). From the optical density (OD) measurements, the myocardial flow was calculated as blood flow: (tissue sample X; mL/min/g)=[withdrawal rate (mL/min)/weight (tissue sample X; g)][OD (tissue sample X)/OD (reference blood sample)], using the Excel worksheet and macros provided by the manufacturer.

Hemodynamic parameters Intravenous infusion caused a mild but significant decrease in blood pressure of 12.3±3.7 mm Hg (p=0.02) in the FGF 2 µg/kg IV group and 9.6±2.1 mm Hg (p=0.01) in the FGF 6 µg/kg IV group. After intracoronary infusion, the drop in blood pressure was significant only at 2 µg/kg with 10.0±2.2 mm Hg (p=0.04) and not at 6 µg/kg (6.1±4.9 mm Hg, p=0.25). In all groups, heart rate decreased mildly, ranging from 2 to 15 bpm, but was significant only in the FGF 2 g/kg IV with 9±4 bpm (p=0.05) and 6 µg/kg IC group with 18±6 bpm (p=0.03).

Coronary angiography Seven follow-up angiograms, two in the control group, two in the FGF 2 µg/kg IV, one in the FGF 6 µg/kg IV, and two in the FGF 2 µg/kg IC group, were not available for analysis. Collateral index had improved significantly in the 6 µg/kg IV group and in both 2 and 6 ug/kg IC groups, whereas baseline collateral index was similar (p=0.119, Kruskal Wallis). For all groups pooled, collateral index resulted from left-to-left collaterals (either LAD to LCX or LCX to LCX, n=37; p<0.001, McNemar test) and not from right-to-left (p=1.0), suggesting a localized effect of intravascular drug delivery. However, changes were not significant in any subgroup.

Coronary blood flow. Baseline regional blood flow in the ischemic (LCX) and normal (LAD) territories was measured at rest and post treatment (final study) at rest and stress (adenosine). Absolute ischemic flow (mL/min/g tissue) and the LCX/LAD flow ratio were determined. LAD flow at baseline, rest, and stress at the final study were similar in the five groups (ANOVA, p=0.363, p=0.418, and p=0.331, respectively). Rest LAD flow did not change significantly over time (ANOVA, p=0.266). In addition, LCX coronary blood flow at baseline (before FGF2 infusion) was similar in all five groups (ANOVA, p=0.361). At the final study at rest, absolute LCX flow and the LCX/LAD ratio did not change significantly. However, LCX flow at stress was significantly higher in the FGF 6 µg/kg IC group than in controls (ANOVA, p=0.039).

Myocardial MRI analysis. Arterial pulse-gated MRI was performed on anesthetized (1% to 2% isoflurane) and ventilated animals, in the body coil of a 1.5-Tesla whole-body (Siemens, Munich Germany) Vision prototype. Baseline anatomic images were obtained by a turboFLASH technique to identify coordinates for apical four-chamber, two-chamber, and short-axis views. For function studies, 24 sequential image frames were collected over 12 heartbeats during breath-hold using shared-center turboFLASH in each of the three standard views. After detection of the optimal inversion time (TI; typically 200 to 300 ms), a series of 32 diastolic images were acquired in the double-oblique four-chamber view during breath-hold, while injecting 0.05 mmol/kg gadodiamide (T1-reducing contrast agent). The series of images was viewed as a movie, to locate the zone with impaired contrast arrival. The short axis at the center of that zone (target zone) was prescribed graphically. All measurements were performed by two independent investigators blinded to treatment. Custom-designed software was used to define myocardial borders and measure wall thickness. End-systolic and end-diastolic left ventricular volumes were computed from biplane measurement (apical four-chamber and two-chamber views) as previously validated, and used to calculate left ventricular ejection fraction. Target wall motion (radial shortening) and target wall thickening were expressed as percentage of the radial length or wall thickness at the end of diastole. Both parameters were also measured at the septum, yielding normal target wall motion and target wall thickening. The area of delayed contrast arrival was defined as myocardium demonstrating distinctly slowed time (.gtoreq.1 cardiac cycle) to half-maximal signal intensity, using a two-dimensional map of contrast intensity versus time.

MRI: left ventricular function Infarct size visualized as myocardium without MRI contrast uptake was measured to avoid confounding of regional function and perfusion measurements. Infarct size was similar among the five groups at either baseline (3 weeks) or final study (ANOVA, p=0.594 and p=0.303, respectively). Infarct size, 3.0%.+−.4.9% left ventricular area (mean±SD), was within the range reported for this model.

Left ventricular ejection fraction (EF) at baseline was similar for all treatment groups (ANOVA, p=0.120). Using each animal as its own control, EF improved significantly in controls (p=0.018), in the FGF 2 µg/kg IV (p=0.046), the FGF 6 µg/kg IV (p=0.001), and the FGF 6 µg/kg IC groups (p=0.001). The improvement in EF after treatment was significantly higher in the FGF 6 µg/kg IC (p<0.01) group compared with controls. The improvement in indexed target wall motion (target wall motion/normal wall motion) was significant only in the FGF 6 µg/kg IV (p=0.019) and the FGF 6 µg/kg IC groups (p=0.004), whereas indexed target wall thickening improved in the FGF 6 µg/kg IC group (ANOVA, p=0.007 compared with improved target wall thickening in controls, p=0.001).

MRI: perfusion. At baseline, no differences in areas of delayed arrival (ANOVA, p=0.140) or collateral extent (p=0.103) were found between the groups. The size of the zone of delayed arrival decreased in the FGF 6 µg/kg IC (p<0.001), which was significantly different from the change in controls (ANOVA, p<0.001).

Toxicologic assessment of FGF-2 administration. Before treatment and at necropsy, blood samples for hematology, coagulation, and serum chemistry were obtained from at least three fasted animals per group. Hematology parameters included hemoglobin, mean corpuscular hemoglobin concentration, hematocrit, erythrocyte count, total leukocyte count, differential, platelet count, mean corpuscular hemoglobin, and mean corpuscular volume. Serum chemistry included aspartate aminotransferase, alanine aminotransferase, gamma glutyltransferase, alkaline phosphatase, lactate dehydrogenase, total bilirubin, total cholesterol, triglycerides, blood urea nitrogen, creatinine, creatine phosphokinase, albumin, globulin, total protein, electrolytes (Na, K, and Cl), calcium, phosphorus, and glucose.

In addition, for four randomly selected animals in each treatment (not vehicle) group, tissue samples were taken from major organs and processed for histology. Histopathological findings were graded on a scale of 1 to 4 (minimal<mild<moderate<marked), by a veterinary pathologist blinded to treatment.

There were no macroscopic or microscopic lesions related to intravenous or intracoronary administration of FGF-2. Furthermore, no changes in hematological or biochemical parameters were observed in any of the treatment groups.

In this study, in which the efficacy of intravenous and intracoronary delivery of 2 or 6 µg/kg FGF-2 was compared, blood supply to the myocardium, as assessed by the colored microsphere method, was improved by the high-dose (6 µg/kg) intracoronary FGF-2. Although this effect was only significant at stress, the same trend was seen for regional blood flow at rest. Both intravenous FGF-2 doses as well as the 2-µg/kg dose were ineffective. This change in regional blood flow was confirmed by perfusion and collateral-sensitive MRI, and had functional significance because it was accompanied by an increase in EF and improvement in target wall motion and target wall thickening in the high-dose intracoronary group, The effect on EF was added to the natural tendency to grow collaterals and improve perfusion and function of ischemic myocardium.

The current study presents evidence that a single intracoronary injection of 120 to 150 µg FGF-2 improves regional blood flow as well as regional and global cardiac function. The ineffectiveness of intravenous FGF-2 might result from less favorable pharmacokinetics. Several studies have reported a 3- to 10-fold lower recovery of radiolabeled FGF-2 from the myocardium after intravenous administration than after intracoronary injection, which in turn has a lower recovery and shorter redistribution times than intrapericardially delivered FGF-2. FGF-2 might be retained in the myocardium by a high-capacity, low-affinity sink provided by heparin sulfates in the matrix and on the surface of endothelial cells, which are upregulated by ischemia. In addition, expression of FGF-R1 receptors, which are the primary transducers of FGF-2 signaling, is also upregulated by ischemia.

In this animal study, in accordance with the phase I clinical trial, intravenous FGF-2 and 2 µg/kg intracoronary FGF-2 had no major hemodynamic, hematotogic, or biochemical side effects.

Clinical implications If a single intracoronary infusion of FGF-2 proves to be effective in patients with chronically ischemic myocardium, this strategy will greatly increase the number of patients that might benefit from adjunctive growth factor therapy, especially in view of the minimal side effects. Each patient undergoing percutaneous revascularization is a candidate for angiogenic therapy because most interventions are local and aimed at the most severe stenoses in epicardial arteries. The additional benefit of myocardial salvage during reperfusion injury by FGF-2 further emphasizes the potential value of this adjunct pharmacotherapy.

It is concluded that a single 6-µg/kg intracoronary FGF-2 delivery results in-significant improvement in collateralization and regional and global function of chronically ischemic myocardium. A single intravenous infusion of FGF-2 is ineffective in the doses tested. A phase 11 clinical trial of patients with coronary artery disease designed to evaluate this intracoronary therapeutic strategy is currently underway.

EXAMPLE 5

Local Perivascular Delivery of FGF-2

In this trial, patients with a viable and ischemic myocardial area that could not be revascularized were randomized to receive heparin-alginate pellets containing 10 or 100 µg of bFGF or placebo that were placed on the epicardial surface during CABG.

Patient Selection. The study population consisted of patients undergoing CABG at Beth Israel Deaconess Medical Center and Albert Einstein College of Medicine in Boston, Mass. The inclusion criteria included an area of myocardium supplied by a major coronary artery with advanced disease not amenable to bypass grafting or percutaneous intervention, inducible ischemia, and the ability to understand and sign the informed consent and to comply with planned follow-up. Patients with the following criteria were excluded from consideration for the study: absence of inducible ischemia or myocardial viability of the target area, hypertrophic or restrictive cardiomyopathy, left ventricular ejection fraction<20%, significant valvular heart disease, renal dysfunction (serum creatinine>2.5 mg/dL), history of malignancy within the previous 5 years, or unexplained hematological or chemical abnormalities before CABG.

The design and performance of the study were approved by the Food and Drug Administration under an investigator-sponsored investigational new drug (BB-IND 5725). The study was approved by the Committee for Clinical Investigation at both institutions. The first patient was enrolled in September 1996 and the last patient in May 1998.

Patient Population and Enrollment Procedure. Seventy-eight patients scheduled for CABG were screened for enrollment into the study on the basis of an angiogram that showed a major epicardial coronary artery (posterior descending artery, significant diagonal, obtuse marginal, or ramus intermedius branch, or significant posterolateral branch) that was considered by an interventional cardiologist and a cardiothoracic surgeon not involved in the study unlikely to be graftable on the basis of its angiographic appearance (diffusely diseased or heavily calcified). Patients were approached for enrollment in the study, and screening tests were performed to ensure that all eligibility criteria were met, including demonstrable ischemia in the target myocardial area. Forty-six patients who met all eligibility criteria and agreed to participate in the study underwent CABG, during which a noninvestigator cardiac surgeon determined whether the target area was indeed ungraftable. Bypass surgery of the target vessel was performed in 22 cases, and those patients were excluded from additional study. The remaining 24 patients (19 patients at Beth Israel Deaconess Medical Center and 5 at Montefiore Medical Center, Bronx, N.Y.) who had a coronary artery that could not receive a graft at the time of surgery were randomized to receive 10 heparin-alginate pellets containing placebo or 1 of 2 doses of bFGF (10 or 100 µg). There was no significant difference between the study groups in any of the clinical parameters, including the extent of coronary disease or presence of any risk factor, except that patients in both 10- and 100-µg bFGF treatment groups were somewhat older than controls, and there were more women in the 10-µg bFGF group. The baseline resting ejection fraction was 50.3±13.8%, and 5 of the 24 patients had an ejection fraction<30%.

Preparation of bFGF-Containing Heparin-Alginate Pellets. Calcium alginate pellets provide a stable platform for bFGF because of enhanced retention of activity and storage time and thus were used as devices for controlled bFGF release in vivo. Heparin-sepharose beads (Pharmacia LKB) were sterilized under ultraviolet light for 30 minutes and then mixed with filter-sterilized sodium alginate. The mixed slurry was dropped through a needle into a beaker containing a hardened solution of $CaCl_2$ (1.5% wt/vol). Beads formed instantaneously. Uniformly cross-linked capsule envelopes were obtained by incubating the capsules in the $CaCl_2$ solution for 5 minutes under gentle mixing and then for 10 minutes without mixing. The beads were washed with sterile water and stored in 0.9% NaCl-1 mmol/L $CaCl_2$ at 4° C. bFGF loading was performed by incubating 10 capsules in 0.9% NaCl-1 mmol/L $CaCl_2$-0.05% gelatin with 12.5 p (for 10-µg dose) or 125µ (for 100-µg dose) of bFGF (GMP grade human recombinant bFGF provided by Scios, Inc.) for 16 hours under gentle agitation at 4° C. Previous studies have shown that under these conditions, 80% of bFGF in solution is absorbed into heparin-alginate pellets. The end product was sterilized under ultraviolet light for 30 minutes. With each preparation, several beads were cultured to ensure sterility. Blank or bFGF-loaded pellets were identical in appearance, which ensured that the surgeons and investigators were blinded with regard to which pellet was being used.

bFGF Heparin-Alginate Delivery After completion of coronary bypasses to all areas of the heart that could be revascularized and failure to graft the target vessel (which on occasions involved probing of the target vessel), multiple linear incisions were made in the epicardial fat surrounding the target vessel. Heparin-alginate pellets (containing bFGF or placebo) were inserted into the epicardial fat overlying the artery and secured in place by a 6.0 prolene suture to close the subepicardial incision. A total of 10 pellets were used in each patient (2 to 3 pellets were placed in each incision). The left internal mammary artery (LIMA) was placed on the left anterior descending artery (LAD), and proximal vein-to-aorta anastomoses were constructed. Ventilation was reestablished, and cardiopulmonary bypass was terminated. Routine closure was then performed.

Short-Term Results. The extent of CABG surgery was the same in all treatment groups; there were no significant differences with regard to the number of grafts, duration of surgery (average 3.0±0.9 hours), or cross-clamp time (average 56±13 minutes). The target vessel was the right coronary artery (RCA) in 15 patients, left circumflex artery in 7, and diagonal branch of the LAD in 2.

One patient in the control group died 24 hours after surgery secondary to an autopsy-documented occlusion of one of the saphenous vein grafts, with a large myocardial infarction in that territory. A second death occurred in a patient in the 100-µg bFGF group who could not be weaned off cardiopulmonary bypass (preoperative ejection fraction of 20%); an autopsy revealed patent grafts with extensive myocardial scarring and a thin rim of epicardial viable myocardium. Two other patients (both in the control group) required intra-aortic balloon pump support after surgery (in 1 patient, the intra-aortic balloon pump was inserted before surgery). Two patients (1 in the control group and 1 in the 10-µg bFGF group) had a Q-wave myocardial infarction in the target myocardial distribution, and 1 patient in the 10-µg bFGF group had a Q-wave myocardial infarction in a nontarget myocardial distribution.

Placement of bFGF-containing heparin-alginate microspheres had no significant short-term effects on blood pressure or heart rate; the mean arterial pressure was 84.8.+−.10.6 mm Hg before bypass, 89±12 mm Hg on day 1, 93±7 mm Hg on day 3, and 83.4±11.1 mm Hg on day 5 and was not different among the treatment groups. Pharmacokinetic evaluation did not reveal any significant increase in serum bFGF levels above baseline in any of the groups (average bFGF levels in 15 patients: 17.4±3.3, 15.90±1.4, 15.9±1.8, and 16±1.8 ug/mL at baseline and postoperative days 1, 3, and 5, respectively), and there were no significant differences in bFGF levels between the different treatment groups. The average postoperative hospital stay was 5.30±1.3 days (range 4 to 8 days). There were no acute effects on serum chemistries, hematologic and coagulation profiles, liver function tests, or urinalysis. Two patients developed superficial wound infections along the chest incision that necessitated surgical debridement, and another patient with diabetes mellitus had delayed healing of the saphenous vein graft harvest site. Microbiological evaluation of the beads showed no aerobic or anaerobic growth in samples from 28 of the 46 preparations.

In-Hospital Follow-Up. The postoperative course was evaluated, including-hemodynamic parameters, duration of ventilatory support, postoperative ECGs, postoperative cardiac isoenzymes, duration of hospitalization, and any evidence of infection. Serum bFGF levels were measured (ELISA, R&D Systems) before implantation and on the first, third, and fifth postoperative days. Complete blood count, coagulation parameters, serum chemistries, and urinalysis were performed before treatment and at days 3 and 5 after treatment. In the first 10 patients, stress nuclear perfusion imaging and MRI (at the Beth Israel Deaconess Medical Center) were performed before CABG; however, owing to the confounding effect of CABG (realized after an interim analysis of the first 10 patients by the Data Safety and Monitoring Committee), the remaining patients underwent stress nuclear perfusion scans (rest-thallium/dipyridamole sestamibi) and MRI after CABG (before discharge). The surgeon, other investigators, and patients were blinded to treatment assignment.

Long-Term Follow-Up. All patients were contacted by the investigators at 6 weeks; 2, 3, 4, and 6 months; 1 year; and then yearly thereafter to assess clinical events (death, myocardial infarction, recurrent angina, or any repeat revascularization). Complete blood count, coagulation parameters, serum chemistries, urinalysis, and serum bFGF level measurements were repeated at 3 months. Patients underwent stress nuclear scans at 3 months (dual-isotope studies with rest thallium and stress [pharmacological stress with dipyridamole sestamibi]). In addition, patients at the Beth Israel Deaconess Medical Center underwent repeat MRI 3 months after CABG. Clinical follow-up of .gtoreq.6 months was available for all patients, with a mean follow-up of 16.0±6.8 months. Clinical Follow-Up. Clinical follow-up was available in the 22 surviving patients (7 from the placebo group, 8 from the 10 µg-bFGF group, and 7 from the 100 µg-bFGF group) and averaged 16.0±6.8 months. At last follow-up, all patients were angina-free except for 3 patients in the placebo group (Canadian Cardiovascular Society [CCS] class II in 1 and class III in 2 patients) and 1 patient in the 10-µg bFGF group (CCS class II). Two of the 3 placebo patients with angina underwent successful percutaneous revascularization (1 involved the target vessel and the second involved a vein graft stenosis). After hospital discharge, none of the patients died or sustained a myocardial infarction. There were no delayed wound infections, no clinical evidence of pericarditis, and no other adverse events. Laboratory evaluation at 90 days (available in 21 patients) did not show any adverse effect on complete blood count, coagulation parameters, serum chemistries, or urinalysis.

Imaging Studies. Rest thallium/dipyridamole sestamibi studies were performed according to the ADAC protocol. We compared baseline and 90-day nuclear scans using the size of the stress perfusion defect, as determined by pixel analysis. MRI was performed in the body coil of a 1.5-T whole-body Siemens Vision system. Baseline anatomic images were obtained by a turboFLASH (turbo Fast Low-Angle SHot) technique to identify coordinates for apical 4-chamber, 2-chamber, and short-axis views. Functional imaging was performed during breathhold by use of shared-center turboFLASH in each of the 3 mutually perpendicular standard views, producing 24 sequential image frames each, collected over 12 heartbeats to measure regional wall motion. MR perfusion imaging was performed as follows: a series of 4 inversion recovery images (1 every second heartbeat) was obtained as inversion time (TI) and adjusted to minimize the signal intensity from myocardium in the fourth frame. With the best TI determined by these scout images, a series of concurrent parallel images were acquired in diastole during breathhold, 1 every other heartbeat, at baseline and again with contrast injection (0.05 mmol/kg gadodiamide). In addition, complete blood count, coagulation parameters, serum chemistries, urinalysis, and serum bFGF level measurements were repeated at 3 months.

Nuclear Perfusion Imaging. Twenty of the surviving 22 patients underwent stress nuclear perfusion imaging 90 days after CABG. In the first 10 patients, baseline studies were performed before CABG. It became clear as the study progressed, however, that this was not a true baseline because of the confounding effect of CABG. Therefore, in the remaining 12 patients, rest-thallium/dipyridamole sestamibi nuclear testing was performed after CAB G and before hospital discharge. The baseline stress target area defect size was 20.6±5.2% of the left ventricle and was similar in all 3 treatment groups (22.3±5.4% in controls, 19.2±5.0% for the 10-µg bFGF group, and 20.4±5.7% for the 100-µg bFGF group, ANOVA P=0.56). At the time of follow-up nuclear scans, when paired t tests were used, there was a trend toward worsening (increase in the defect size) in the placebo group (20.7±3.7% at baseline to 23.8±5.7% at follow-up, P=0.06). Studies in the 10-µg bFGF group showed no change in defect size (19.2±5.0% to 16.9±8.1%, P=0.39), whereas defect size in the 100-µg bFGF group was significantly improved compared with baseline (19.2±5.0% to 9.1±5.9%, P=0.01). The change in defect size was significantly different among the 3 groups (ANOVA P=0.005). Semiquantitative analysis of stress images demonstrated worsening of the defect in 3 of 6 patients and no change in 3 of 6 patients in the control group. Of 8 patients in the 10-ug bFGF group, the target nuclear defect size worsened in 2 patients, remained unchanged in 2, and improved in 4. Finally, of the 6 patients in the 100-µg bFGF group who underwent follow-up nuclear testing, there was improvement in 5 patients and no change in 1 patient.

Magnetic Resonance Imaging. Functional and perfusion MRI were performed in 8 patients at the Beth Israel Deaconess Medical Center at baseline and at 90-day follow-up (4 controls and 4 bFGF-treated patients [1 patient in the 10-µg bFGF group and 3 in the 100-µg bFGF group]). Baseline resting target wall motion (radial wall motion) was 21.7±6.7% in the placebo group and 27.3±17.0% in patients treated with 100 µg of bFGF (compared with 35.7±10.9% for normal revascularized wall). No changes in resting target wall motion were seen at follow-up (23.7±9.3% in placebo and 32.3±12.4% in 100-µg bFGF-treated subjects). The extent of the resting delayed contrast arrival zone, which reflects underperfused myocardium, for placebo and bFGF-treated patients was 10.7±3.9% and 15.7±2.3% at baseline and decreased to 7.8±6.9% (P=0.37) and 3.7±6.3% (P=0.06) at follow-up, respectively, with a trend toward improvement in the 100-µg bFGF group.

Because of the protracted course of new collateral development, the potential for hemodynamic disturbances associated with bolus intravascular delivery, and the possibility for toxicity from elevated circulating levels of angiogenic growth factors, a local sustained bFGF delivery strategy using heparin-alginate microcapsules was used. This delivery system allows prolonged (4 to 6 weeks) sustained release (first-order kinetics). In animal studies, there was a dose-dependent effect of bFGF that was not associated with detectable serum levels, hemodynamic effects, or locator systemic toxicity.

Of the 46 patients judged to have a major coronary artery that could not be grafted on the basis of angiographic appearance, 22 patients were actually successfully grafted at the time of CABG. Thus, preoperative assessment of arterial suitability for bypass proved to be inaccurate in almost 50% of cases. In accordance with prior observations, the major epicardtal artery most likely to be unsuitable for grafting was the RCA. In no case was the LAD considered ungraftable. This paucity of LAD cases is probably a reflection of the reluctance to refer those patients in whom the LAD may not be bypassed for surgical intervention.

The combination CABG/bFGF therapy was not associated with an excess rate of complications. Two operative deaths in this study most likely reflect the higher operative risk in patients with advanced coronary disease and left ventricular dysfunction who have incomplete revascularization. The absence of hemodynamic abnormalities associated with heparin-alginate bFGF delivery is consistent with the undetectable serum levels of bFGF at any time after growth factor administration. In addition, the lack of short- or intermediate-term adverse effects on serum chemistries, hematologic profile, liver function tests, or urinalysis also suggests that this mode of delivery is not associated with systemic toxicity. These observations therefore emphasize the safety of heparin-alginate bFGF delivery at the time of CABG.

This randomized, double-blind, placebo-controlled study of bFGF in patients undergoing CABG demonstrates the safety and feasibility of this mode of therapy in patients with viable and isohemic but unrevascularizable myocardium. These results warrant a larger multicenter trial to assess the clinical benefit of this combination approach to myocardial revascularization, which is currently under way.

EXAMPLE 6

Reduction in Myocardial Infarct Size Following Intracoronary Administration of FGF-2

The extent of myocardial injury and necrosis resulting from an ischemic insult is determined by the duration of interruption to antegrade flow, the size of the compromised territory, and the extent of collateral circulation to the region. In view of the beneficial effects on myocardial viability and contractile function demonstrated in collateralized patients with occlusive coronary artery disease, these findings provide a rationale for investigation of new strategies that use growth factors such as bFGF to pharmacologically enhance collateral growth and to blunt the effects of impaired antegrade myocardial perfusion.

Coronary Occlusion and Reperfusion. Twenty-two mongrel dogs of either sex (weight, 17 to 23 kg) were randomly assigned to treatment with bFGF or vehicle. After the animals received anesthesia with sodium pentobarbital (25 mg/kg IV), intubation, and ventilation with room air, the right carotid artery was exposed, ligated distally, and cannulated. Aortic blood pressure, heart rate, and ECG were monitored continuously throughout the procedure. After baseline left ventriculography was accomplished via a 6F pigtail catheter, selective left coronary angiography was performed via an 8F angioplasty guiding catheter. Because of the potential interaction between heparin and bFGF, intraprocedural anticoagulation was achieved with the use of Hirulog, a synthetic direct thrombin inhibitor; after an intravenous loading dose of 2.5 mg/kg, intravenous infusion was commenced at 5 mg.multidot.kg$^{-1}$.multidot.h$^{-1}$ and the rate adjusted to maintain the activated clotting time at >300 seconds.

An angioplasty balloon catheter (balloon:artery ratio 1.0) was then inflated at 2 atm in the middle part of the LAD distal to the first diagonal branch, and occlusion was confirmed angiographically. After 4 hours' occlusion, the balloon catheter was deflated and removed, and LAD patency was confirmed angiographically. Ten micrograms of human recombinant bFGF (in 20 mmol/L sodium citrate, 1 mmol/L EDTA, and 9% sucrose, pH 5; Scios Nova Inc.) in 10 mL normal saline or vehicle (10 mL normal saline) was administered directly into the left main coronary artery via the guiding catheter 10 minutes after occlusion and again just before reperfusion. After reperfusion, left ventriculography was repeated. All surgical procedures were performed with the use of a sterile technique. Seven days after the first procedure, dogs were anesthetized, intubated, and ventilated in the same manner as before. Patency was confirmed angiographically, left ventriculography was repeated, and euthanasia was performed with a lethal dose of pentobarbital.

Occlusion-Reperfusion Study. Blood pressure and heart rate were similar in both groups throughout the experiment. Heart rate was increased during reperfusion in vehicle- and in bFGF-treated dogs (both P=0.043 versus baseline) because of nonsustained ventricular tachycardia and frequent ventricular ectopic activity. No systemic hemodynamic changes were noted after bFGF was administered. The areas at risk were similar in both groups (41±8 cm$^2$ versus 40±6 cm$^2$, vehicle versus bFGF). In the bFGF-treated group, infarct size expressed as a percentage of the area at risk was 13.7±2.1%, which was significantly less than in dogs receiving vehicle (28.4±3.4%; P=0.002; FIG. 3*). At baseline, left ventricular ejection fractions were similar in both groups (bFGF versus vehicle, 42.6±1.9% versus 44.8±3.5%). After reperfusion (bFGF versus vehicle, 33.1±5.4% versus 40.3±3.2%) and again at 1 week after infarction (bFGF versus vehicle, 33.6±3.6% versus 38.8±3.5%), ejection fractions showed no significant difference between groups (FIG. 4*).

Microscopic examination of sections demonstrated concordance between triphenyltetrazolium chloride infarct delineation and histological features of myocardial necrosis.

Although bFGF treatment was associated with significant myocardial salvage, there was no difference in the number of endothelial cells per high-power field within the infarcted region (bFGF versus vehicle, 241±16 versus 221±18 cells/hpf; P=0.8) or in the number of endothelial cells in the border zones (bFGF versus vehicle, 247±18 versus 245±15 cells/hpf; P=0.63). Because of the potential for spurious PCNA counts in areas of leukocyte infiltration, PCNA counts were obtained from border zones only; these counts were similar in both groups (bFGF versus vehicle, 10.1±2.3 versus 7.3±2.3 cells/hpf; P=0.4).

Measurement of Activated Clotting Time. Activated clotting time was measured with the use of the Hemochron 801 timer (International Technidyne Corp). After 2 mL of whole blood was collected into a Hemochron tube containing 12 mg of Johns-Manville diatomaceous earth, the time taken to complete coagulation at 37° C. was measured.

Delivery and Biological Activity of bFGF. To ensure delivery of bFGF after passage through the manifold and angioplasty guiding catheter, radiolabeled bFGF was passed through new and used systems. To simulate the conditions of an in vivo experiment, 20 μg of cold bFGF was mixed with 25 μCi of radiolabeled bFGF in 20 mL of normal saline solution. A second batch of 20 μg of cold bFGF was mixed with 25 μCi of radiolabeled bFGF in 20 mL of normal saline solution containing 1 mg/mL of dog albumin (Sigma Chemical Co). The number of counts per minute from both solutions was quantified in a scintillation counter. Ten-milliliter aliquots of the radiolabeled solutions were then delivered through used and new guiding catheters and manifolds and flushed with an additional 10 mL of normal saline. The number of counts per minute in the solutions collected after passage through the catheter system was measured. The difference in counts per minute between the incoming and outgoing solution was used as an index of bFGF loss within the delivery system. Under the conditions described above, there was minimal loss of activity in the delivery system. The bFGF used in the experiments was compared in a mitogen assay with human recombinant bFGF from a commercial source (Boehringer Mannheim) that had proven activity in previous assays. The potency of both lots of bFGF was similar, as assessed by $^3$H-thymidine uptake after stimulation of cultured human fibroblasts (data not shown).

Determination of Infarct Size. After euthanasia and rapid excision of the heart, the LAD and circumflex arteries were cannulated individually. Simultaneously, at a pressure of 100 mm Hg, the circumflex vessel was perfused with Evans blue dye and the LAD with triphenyltetrazolium chloride for 10 minutes. Hearts were then fixed by perfusion with Histo-Choice (Ameresco) for 4 hours, after which the left ventricle was cut into 1-cm-thick slices perpendicular to its long axis, and the slices were weighed. With this technique, areas of viable tissue in the LAD distribution are stained red, necrotic areas remain white, and the circumflex territory is stained blue. For each slice, the area at risk, the area of infarction, and the circumflex territory were determined by computer-assisted planimetry, as previously described.

Histology and Immunohistochemistry. Multiple tissue samples were taken from areas of infarction and areas at risk of infarction for histological examination to seek evidence of neovascularization. Given the assumptions that (1) neovascularization of ischemic regions would proceed from the circumflex and nonoccluded LAD distributions and (2) the tissue stimulus for neovascularization would be intense in tissue adjacent to the infarct zone, "border-zone" samples were taken from the area at risk midway between the edges of the macroscopically infarcted myocardium and the junction of the LAD and circumflex territories. Staining with hematoxylin and eosin was used to confirm the presence of tissue necrosis in the infarct zones. Immunohistochemical staining of tissue samples was performed with factor VIII-related antigen to detect endothelial cells and PCNA to detect proliferating cells.

After being embedded in paraffin, 5-um sections were cut and collected onto glass slides coated with 1% polychloroprene in xylene. After being dried for 60 minutes at 60° C., paraffin was removed in three changes of xylene. The tissue was then rehydrated through graded alcohols before being rinsed in PBS. Immunohistochemical staining was performed in a Jung Histostainer (Leica). A 0.6% hydrogen peroxide solution in PBS was then applied for 5 minutes to remove any endogenous peroxidase. For the PCNA sections, a blocking solution of 1:10 (vol/vol) normal rabbit serum (Dako Corp) was added for 10 minutes before application of a 1-in-50 dilution of murine monoclonal antibodies directed against PCNA (PC10 Clone, Dako Corp). For the factor VIII-related antigen stain, a blocking solution of 1:10 (vol/vol) normal swine serum (Dako Corp) was added for 10 minutes before application of a 1:300 dilution of rabbit polyclonal antibodies directed against factor VIII-related antigen (Dako Corp). The dilutions of the primary antibodies were prepared with the use of 1% BSA in PBS and were incubated with the tissue sample at 30° C. for 60 minutes. A 1:200 dilution of biotinylated rabbit anti-mouse polyclonal antibody (Dako Corp) was then added for 30 minutes to the PCNA sections, and 1:200 biotinylated swine anti-rabbit polyclonal antibody (Dako Corp) was added to the factor VIII-stained sections for 30 minutes. These antibodies were labeled with an Elite streptavidin-biotin-peroxidase complex (Vector Laboratories) applied for 30 minutes. The final stage involved the addition of 3,3'-diaminobenzidine (Vector Laboratories) as a chromogen. Between steps, the sections were rinsed for 2 minutes in PBS. Slides were then rinsed in distilled water, dehydrated, cleared in xylene, and mounted in Permount (Fisher Scientific). In each staining preparation, sections treated with 1% BSA in PBS instead of with the primary antibody were included as negative controls, and sections of human tonsil were used as positive controls.

Cell Counts. Photographs of immunohistochemically stained tissue sections were taken without knowledge of treatment assignment. After low-power examination, five to seven representative fields (0.5×0.34 mm) were photographed from each section at a magnification of 200×. Whenever possible, consecutive adjacent fields were photographed. In sections from the infarct zone, fields with relative preservation of tissue architecture were selected, obviating spurious increases in vessel density due to preservation of vascular structures in areas of parenchymal loss and stromal collapse. Cells that stained positive for PCNA and factor VIII (regardless of the presence of a vascular lumen) were counted by two independent observers blinded to treatment assignment (interob server correlation coefficient, r=0.69; P<0.0001). Immunostaining for factor VIII and PCNA represented the techniques currently used as diagnostic tools for measurement of tumor angiogenesis.

Left Ventricular Ejection Fraction. Left ventricular ejection fractions were determined from single-plane left ventriculograms measured by a trained technician who was blinded to treatment assignment. Ejection fractions were calculated by use of the length-area method with a computer analysis package (Angiographic Ventricular Dynamics 5.1, Siemens).

Acute Hemodynanlic Studies In five additional dogs of either sex (weight, 19 to 22 kg), we compared the effects of intracoronary bFGF on coronary hemodynamic parameters with those of temporary coronary occlusion and intracoronary NTG. The studies were performed with the use of a standard open-chest model in which the LAD was isolated and instrumented with a Doppler flow probe to measure blood flow (Crystal Biotech). A 2F catheter was advanced retrogradely via a small proximal branch of the LAD into the left main vessel for administration of drugs. Blood flow responses after 10- and 20-second periods of LAD occlusion and after incremental doses of intracoronary NTG (1, 10, and 100 ug) were recorded to confirm the presence of coronary vascular reactivity. Incremental doses of intracoronary bFGF (1, 10, and 100 ug) were then given, and coronary flow responses were measured. bFGF (buffered as described above) and NTG solutions were prepared in 1 mL of normal saline just before administration and were given as boluses over 20 seconds. Blood pressure, heart rate, and ECG were monitored continuously throughout the procedure. Coronary vascular resistance (CVR) was calculated according to the formula:

$$\text{CVR (mmHg.multidot.mL}^{-1}) = \text{mean aortic pressure (mm Hg)} \times 1/(\text{coronary flow (mL/min)})$$

The results of the occlusion-reperfusion study demonstrated a reduction in infarct size without histochemical evidence of myocardial neovascularization. The acute hemodynamic study was performed to assess the presence of a vasodilator action of bFGF as described in dogs and other species whereby flow to the infarct zone could possibly be augmented by an increase in the conductance of preexisting collateral channels, independently of neovascularization. In the five dogs studied, coronary blood flow and coronary vascular resistance were unchanged after incremental pharmacological doses of intracoronary bFGF despite pronounced vasodilator responses to 10- and 20-second coronary occlusion and intracoronary NTG. In addition, three of the dogs were monitored for 30 minutes after the final dose of bFGF (100 µg) to detect the presence of a delayed vasodilator response as reported previously. No significant hemodynamic changes were observed in response to bFGF during the experiment.

Institutional Approval and Sample Size. The protocol was approved by the Cleveland Clinic Foundation Institutional Review Board and Animal Research Committee. Animals were handled in accordance with the National Institutes of Health guidelines for the use of experimental animals. In the occlusion-reperfusion study, 22 dogs were randomized to receive bFGF or vehicle. Five dogs (2 treated with bFGF, 3 with vehicle) died of arrhythmias before completion of the protocol. Three dogs (1 treated with bFGF, 2 with vehicle)

were excluded because of persistent occlusion at the site of balloon occlusion. No dogs were excluded from the acute hemodynamic study.

Data Analysis. All data are expressed as mean±SEM. Differences between groups were evaluated by use of two-tailed, unpaired t tests. The Pearson correlation coefficient was used to assess inter-observer variability for cell counts. Repeated measurements of left ventricular ejection fraction were compared by use of two-way ANOVA. Differences were considered significant at a value of P<0.05.

This study has demonstrated that bFGF reduces the extent of infarction in the canine occlusion-reperfusion setting. Although there is little doubt that the beneficial effects of bFGF on coronary perfusion in chronic ischemia are mediated principally by its angiogenic actions, we have demonstrated that myocardial salvage occurs independently of neovascularization after administration of bFGF in the setting of acute myocardial infarction. Further evaluation of coronary vasomotor responses to bFGF in ischemic and nonischemic settings and investigation of the potential cytoprotective properties of bFGF in acute ischemia promise to provide fertile and clinically relevant areas for future investigation.

EXAMPLE 7

Intracoronary and Intravenous Administration of FGF-2

This study was designed to investigate the myocardial and tissue deposition and retention of bFGF after IC and IV administration in normal and chronically ischemic animals.

Tissue distribution studies were carried out in 24 Yorkshire pigs (12 normal animals and 12 chronically ischemic animals). Yorkshire pigs of either sex weighing 15 to 18 kg were anesthetized with IM ketamine (10 mg/kg) and halothane inhalation anesthesia. By sterile technique, a right popliteal cut down was performed and a 4 French arterial catheter was inserted for blood sampling and pressure monitoring. Left thoracotomy was performed through the 4th intercostal space during mechanical ventilation. The pericardium was opened and an ameroid constrictor of 2.5 mm internal diameter (matched to the diameter of the artery) was placed around the proximal left circumflex coronary artery. The pericardium was closed using 6/0 Prolene and the chest was closed. A single dose of IV cefazolin (70 mg/kg) was given and IM narcotic analgesics were administered as needed. Animals were then allowed to recover for 3 weeks (time sufficient for ameroid closure) before radiolabeled growth factor delivery. The treatment of animals was done according to National Institutes of Health guidelines and the protocol was approved by the Institutional Animal Care and Utilization Committee of the Beth Israel Deaconess Medical Center.

A total of 24 animals were used for the study. Twelve animals underwent ameroid placement on the LCX, and 3 weeks later, after confirming LCX occlusion angiographically, received $^{125}$I-bFGF. IC $^{125}$I-bFGF was administered to six normal and six ischemic animals, whereas IV $^{125}$I-bFGF was given to six normal and six ischemic animals. Tissue deposition was measured at 1 and 24 h in three animals of each group. The use of these two time points was determined by the need to study more sustained myocardial deposition and retention of $^{125}$I-bFGF.

Ischemic animals (three weeks after ameroid placement) and normal noninstrumented animals were anesthetized with IM ketamine (10 mg/kg) and halothane inhalation anesthesia. By sterile technique, an IV line was inserted into the ear vein and a right femoral cut down was performed to introduce an 8 Fr arterial sheath. Coronary angiography was then performed in multiple views using a 7 French JR4 diagnostic catheter (Cordis Laboratories, Inc., Miami, Fla.) to confirm LCX occlusion in ischemic animals and to assess the coronary anatomy. $^{125}$I-Bolton Hunter-labeled bFGF ($^{125}$I-bFGF; 25 µCi; New England Nuclear) with a specific activity of 110 µCi/ug (4050 kBq/µg) was combined with 30 µg of cold bFGF and 3 mg of heparin (similar to the dose used in animal studies and in the recent phase I IC and IV human study) and was used for IC (six normal and six ischemic animals) and IV (six normal and six ischemic animals) delivery. For IC delivery, $^{125}$I-bFGF was infused in the left main coronary artery over 10 min. For IV delivery, $^{125}$I-bFGF was infused through the ear vein IV line over 10 min. Animals were then sacrificed 1 (n=12) and 24 h (n=12) after $^{125}$I-bFGF administration.

Extracardiac Deposition. Biodistribution of the IV and IC radiolabeled bFGF was determined at 1 and 24 h after administration and was pooled for ischemic and nonischemic animals. There were no significant differences between ischemic and nonischemic animals at each time point and the data was therefore pooled. At 1 h, the liver accounted for 37.6±17.1% of the total administered activity for IC and 42.1±17.7% for IV delivery (p=0.6), with a reduction to 2.8±1.5% for IC and 1.5±0.9% for IV delivery by 24 h (p=0.09). Total specific activity (1 h) in the kidneys was 2.3±1.3% for IC and 2.5±1.0% for IV delivery (p=0.8). By 24 h, total kidney specific activity decreased to 0.1±0.05% for IC and 0.2±0.09 for IV delivery (p=0.1). Finally, for IC and IV delivery, total lung specific activity was 2.7±4.1 and 3.8±2.6% at 1 h (p=0.6) and 0.2±0.2 and 0.4±0.08% at 24 h (p=0.05), respectively. Specific activity for urine was 0.01±0.01% for IC and 0.005±0.01% for IV administration at 1 h and increased to 0.02±0.01% for IC and 0.03±0.05% at 24 h for IV delivery, however, that increase was not statistically significant.

Cardiac Deposition. Total specific activity (1 h) was 0.88±0.89% for IC and 0.26±0.08% for IV administration (p=0.12) and decreased to 0.05±0.04% (p=0.05, compared with 1 h values) and 0.04±0.01% (p<0.001, compared with 1 h values) at 24 h, respectively. There were no differences between epicardial and endocardial deposition for both IC delivery; the results were pooled for further analysis. For IC delivery, LAD territory activity per gram of tissue (1 h) was 0.01±0.007% and 0.008±0.008% for normal and ischemic animals, and at 24 h dropped to 0.0005±0.0009% (20-fold reduction) in nonischemic animals and 0.0008±0.0005% (10-fold reduction) in ischemic animals. For IV delivery. 1-h LAD territory activity per gram of tissue was 0.003±0.001% (3-fold reduction, p=0.2, compared with IC) and 0.002±0.0009% (4-fold reduction, p=0.3, compared with IC) for normal and ischemic animals, and at 24 h dropped to 0.0004±0.0001% (7.5-fold reduction) in nonischemic animals and 0.0004±0.0004% (5-fold reduction) in ischemic animals, respectively. For 1-h LCX myocardial deposition, IC and IV deliveries resulted in a specific activity per gram of tissue of 0.008±0.004% and 0.003±0.001% (2.6-fold reduction, p=0.09) in normal animals and 0.01±0.007% and 0.003±0.001% (3.3-fold reduction, p=0.2) in ischemic animals, respectively. At 24 h, LCX deposition for IC and IV delivery dropped to 0.0006±0.0008% and 0.0005±0.0002% in normal animals and 0.0006±0.0006% and 0.0004±0.0004% in ischemic animals, respectively. For all groups, RCA myocardial distribution was similar to LAD and LCX distribution for IV administration. However, for IC delivery, RCA myocardial deposition was significantly lower than LAD or LCX myocardial deposition, because the radiolabel was infused in the left main coronary artery. Finally, for IC delivery, LCX/LAD territory activity was 79% and 154% for nonischemic and isohemic animals at 1 h and 116% and 75% for nonischemic and ischemic animals at 24 h, respectively. Intravenous administration resulted in an LCX/LAD activity of 97% and 100% for nonisohemic and ischemic animals at 1 h and 123% and 98% for nonischemic and ischemic animals at 24 h. respectively.

Myocardial autoradiography confirmed myocardial deposition for both IC and IV delivery with three times enhanced deposition for IC delivery compared with IV delivery at 1 h with near equalization of tissue deposition at 24 h (measured using densitometric analysis). In addition, IC delivery resulted in increased deposition in LAD and LCX deposition compared with RCA (noninfused territory) deposition, whereas IV delivery resulted in a more uniform distribution in the three myocardial territories by qualitative analysis. Light level autoradiography after 72-h exposure showed LAD endothelial deposition for IC delivery after 1 h. Evaluation of other arteries for IC delivery at 24 h and for all coronary arteries at all time points failed to show $^{125}$I-bFGF deposition even after 96 h of exposure.

Duplicate plasma, urine (spot samples), and tissue samples from the liver, lung, kidney, and quadriceps muscle were obtained. Tissues were washed three times in saline to avoid contribution of radioactivity in blood. The heart, liver, lungs, and kidneys were weighed to determine total organ weight. Duplicate samples were also obtained from the right ventricle and from the proximal portion of the left anterior descending coronary arteries (LADs) and right coronary arteries (RCAs). A 1-cm mid left ventricular transverse slice was sectioned and cut into eight segments; each segment was divided into epicardial, mid-myocardial, and endocardial portions. $^{125}$I-bFGF activity was determined in a gamma counter (LKB Instruments, Inc., Gaithersburg, Md.). Background was subtracted and the amount of $^{125}$I-bFGF deposited within a specific sample was calculated as a percentage of the total activity administered. Total solid organ deposition was calculated by multiplying the specific activity per gram of tissue by the weight of the organ. Trichloroacetic acid precipitation was performed to determine specific activity, which averaged 86.3±24.4%. A 2-mm transverse left ventricular section was obtained for organ level autoradiography and exposed in a phosphoimager for 24 h. In addition, tissue samples were obtained from the LAD and the subtended myocardium, formalin-fixed, paraffin-embedded, and 10 um sections were mounted on a slide, coated by a photographic emulsion for 72 h, developed, and examined using light level microscopy.

Data are expressed as mean±S.D. Continuous variables were compared by unpaired Student's t test, whereas categorical variables were compared by $\varkappa^2$ analysis. All reported p values were two-tailed; $p<0.05$ was considered statistically significant.

Both IC and IV delivery strategies resulted in the majority of radiolabel being deposited in the liver. Surprisingly, liver deposition was similar for both techniques, indicating significant recirculation for IC delivery. In addition, these results confirm the previous observation that the liver is the major organ of elimination with circulating bFGF binding to α-2-macroglobulin, which in turn is internalized by receptors on Kupifer. This result was duplicated for renal and lung deposition. It is important to point out that bFGF was infused in the ear vein (above the diaphragm). However, this simulates IV delivery in patients where the port of entry would probably be an upper extremity vein bypassing the liver first pass mechanism. Therefore, IC delivery does not result in less systemic deposition, probably due to high recirculation.

One-hour total and regional myocardial deposition was 3- to 4-fold higher for IC compared with IV delivery, and deposition dropped by 5- to 20-fold at 24 h. IC delivery resulted in higher deposition in ischemic myocardium, possibly related to the increased expression of fibroblast growth factor receptors associated with myocardial ischemia. This was not seen in IV delivery, possibly related to the initial concentrations delivered to the ischemic myocardium. Thus IC delivery, by providing higher initial concentrations in the coronary circulation, may result in higher deposition in ischemic areas. These comparisons, although consistent, did not reach statistical significance due to the small number of animals studied.

Of note, IC delivery resulted in enhanced bFGF deposition compared with IV delivery only in myocardial territories subtended by the infused artery. Therefore, for IC delivery to provide an advantage over IV delivery, infusion should be carried out in all coronary arteries and bypass grafts if present. Whether infusing a larger dose of bFGF would result in similar myocardial deposition to IC delivery (a more invasive approach) was not investigated. For IC delivery, bFGF was identified on the endothelial cells of the infused arteries, where it might exert its effect. In addition, this study raises an important question of whether more local or sustained delivery is necessary for bFGF effect, particularly with the relatively low cardiac deposition for both delivery modalities.

EXAMPLE 8

The patient is a two year old girl who suffered a stroke at birth and was diagnosed with cerebral palsy. She is given an IV infusion comprising stem cells derived from her own cord blood. Her parents notice improvements within a few days of the infusion; they inform her physicians that she is now able to say her nickname, which she had not been able to do prior to the infusion. Physicians estimate that the patient has regained 50% of her faculties.

Note: The above example prompted Phase I and Phase II clinical trials (NCT01072370) entitled: "A Placebo-Controlled, Observer-Blinded, Crossover Study to Evaluate the Safety and Effectiveness of a Single, Autologous, Cord Blood Stem Cell Infusion for the Treatment of Cerebral Palsy in Children.

Source: ww HYPERLINK "http://www.clinicaltrials.gov/ct2/show/NCT01072370"w HYPERLINK "http://www.clinicaltrials.gov/ct2/show/NCT01072370".clinicaltrials.gov/ct2/HYPERLINK "http://www.clinicaltrials.gov/ct2/show/NCT01072370"s HYPERLINK "http://www.clinicaltrials.gov/ct2/show/NCT01072370"how/NCT01072370

EXAMPLE 9

A study was conducted at the Center of Excellence for Aging and Brain Repair, University of South Florida College of Medicine, Tampa, Fla. Intravenous delivery of human umbilical cord blood cells (HUCBC) 48 hours after a middle cerebral artery occlusion (MCAo) in a rat resulted in both behavioral and physiological recovery. Nissl and TUNEL staining demonstrated that many of the neurons in the core were rescued, indicating that while both necrotic and apoptotic cell death occur in ischemia, it is clear that apoptosis plays a larger role than first anticipated. Further, immunohistochemical and histochemical analysis showed a diminished and/or lack of granulocyte and monocyte infiltration and astrocytic and microglial activation in the parenchyma in animals treated with HUCBC 48 h poststroke. Successful treatment at this time point should offer encouragement to clinicians that a therapy with a broader window of efficacy may soon be available to treat stroke. Timing of cord blood treatment after experimental stroke determines therapeutic efficacy.

EXAMPLE 10

A study was conducted at the Department of Neurology, Medical College of Georgia in Augusta, Ga., to investigate the efficacy of intrahippocampal transplantation of multipotent progenitor cells (MPCs), which are pluripotent progenitor cells with the ability to differentiate into a neuronal lineage. Seven-day-old Sprague-Dawley rats were initially subjected to unilateral HI injury, which involved permanent ligation of the right common carotid artery and subsequent exposure to hypoxic environment. At day 7 after HI injury, animals received stereotaxic hippocampal injections of vehicle or cryopre-served MPCs (thawed just prior to transplantation) derived either from Sprague-Dawley rats (syngeneic) or Fisher rats (allogeneic). All animals were treated with daily immunosuppression throughout the survival period. Behavioral tests were conducted on posttransplantation days 7 and 14 using the elevated body swing test and the rotarod to reveal general and coordinated motor functions. MPC transplanted animals exhibited reduced motor asymmetry and longer time spent on the rotarod than those that received the vehicle infusion. Both syngeneic and allogeneic MPC transplanted injured animals did not significantly differ in their behavioral improvements at both test periods. Immunohistochemical evaluations of graft survival after behavioral testing at day 14 posttransplantation revealed that syngeneic and allogeneic transplanted MPCs survived in the hippocampal region. These results demonstrate for the first time that transplantation of MPCs ameliorated motor deficits associated with HI injury. In view of comparable behavioral recovery produced by syngeneic and allogeneic MPC grafts, allogeneic transplantation poses as a feasible and efficacious cell replacement strategy with direct clinical application. An equally major finding is the observation lending support to the hippocampus as an excellent target brain region for stem cell therapy in treating HI injury.

EXAMPLE 11

Another study examined the feasibility, efficacy, and safety of cell therapy using culture-expanded autologous MSCs in patients with ischemic stroke. Thirty patients with cerebral infarcts within the middle cerebral arterial territory and with severe neurological deficits were prospectively and randomly allocated into one of two treatment groups: the MSC group (n=5) received intravenous infusion of $1 \times 10^8$ autologous MSCs, whereas the control group (n=25) did not receive MSCs. Changes in neurological deficits and improvements in function were compared between the groups for 1 year after symptom onset. Neuroimaging was performed serially in five patients from each group. Outcomes improved in MSC-treated patients compared with the control patients: the Barthel index (p=0.011, 0.017, and 0.115 at 3, 6, and 12 months, respectively) and modified Rankin score (p=0.076, 0.171, and 0.286 at 3, 6, and 12 months, respectively) of the MSC group improved consistently during the follow-up period. Serial evaluations showed no adverse cell-related, serological, or imaging-defined effects. In patients with severe cerebral infarcts, the intravenous infusion of autologous MSCs appears to be a feasible and safe therapy that may improve functional recovery. Oh Young Bang, MD, PhD; Jin Soo Lee, MD; Phil Hyu Lee, MD, PhD; Gwang Lee, PhD. *Autologous mesenchymal stem cell transplantation in stroke patients*, Ann Neurol 2005;57:874-882.

EXAMPLE 12

Another study tracked the transplanted cells in vivo by magnetic resonance imaging (MRI) scans and validated the results by histology. MSCs went through a two-step medium-based differentiation protocol, followed by in vitro characterization using immunocytochemistry and immunoblotting analysis of the cell media. The migratory properties of the cells were examined in the quinolinic acid (QA)-induced striatal lesion model for Huntington's disease. The induced cells were labeled and transplanted posterior to the lesion. Rats underwent serial MRI scans to detect cell migration in vivo. On the 19th day, animals were sacrificed, and their brains were removed for immunostaining. Rat MSCs postinduction exhibited both neuronal and astrocyte markers, as well as production and secretion of NTFs. High-resolution two-dimensional and three-dimensional magnetic resonance images revealed that the cells migrated along a distinct route toward the lesion. The in vivo MRI results were validated by the histological study, which demonstrated that phagocytosis had only partially occurred and that MRI could correctly depict the status of the migrating cells. The results show that these cells migrated toward a QA lesion and therefore survived for 19 days posttransplantation. This gives hope for future research harnessing these cells for treating neurodegenerative diseases. Sadan, O; Shemesh, N; Barzilay, R; Bahat-Stromza, M; Melamed, E; Cohen, Y; and Offen, D. *Migration of Neurotrophic Factors-Secreting Mesenchymal Stem Cells Toward a Quinolinic Acid Lesion as Viewed by Magnetic Resonance Imaging*. Stem Cells Vol. 26 No. 10 October 2008, pp. 2542-2551.

EXAMPLE 13

A sixty (60) year old male patient suffers from acute coronary ischemia. He has had three (3) MI's and now suffers from CHF. He has an ejection fraction of 19%. He is monitored by his physician and has recurring angina and SOB. Bone Marrow is collected from his right hip using thin-needle micropuncture under local anesthesia. The entire procedure takes 30 min. The stem cells are processed from the bone marrow in a lab. There are 3.1 million CD 34+ cells. 80% are viable. The stem cell volume is four (4) ml. Two (2) days later the stem cells are implanted into his heart via a catheter. The patient is hospitalized and connected to a heart monitor for 1 night. At 4 am the patient wakes up and performs 4 push-ups! He is not lightheaded. Six (6) months later his ejection fraction is 45-55%. He has no angina and no SOB. After discussion with his physician it is decided to have no further stem cell treatments at this time. He is satisfied with his current progress.

EXAMPLE 14

A forty five (45) year old female smoker has an ankle brachial index (ABI) of 0.84. She receives an effective dose of stem cells derived from cord blood by IV. One year later she has an ABI of 0.85. She was pleased with her progress and no further stem cell treatments were performed.

EXAMPLE 15

Seventeen (17) patients have an average occlusion of the internal carotid arteries of 23.5% measured by US. Their average Hemoglobin A1c is 7.2. Their average total cholesterol is 205. Six (6) patients receive an effective dose of stem cells derived from cord blood and cord tissue by IV. Six (6) patients receive a similar volume of normal saline by IV. Five (5) patients receive 75 mg of Plavix and 10 mg of Lipitor daily for 1 year. After 1 year the group that received the stem cells has an average occlusion of 25%, and average A1c of 7.0, and an average total cholesterol of 200. The group with the normal saline has an average occlusion of 29%, an average A1c of 7.4, and an average total cholesterol of 217. The group with Plavix and Lipitor has an average occlusion of 27%, and average A1c of 7.2, and an average total cholesterol of 194.

EXAMPLE 16

Fourteen (14) patients have an average 45% occlusion of the LAD by coronary angiogram. There average total cholesterol is 217. Five (5) patients receive an effective dose of stem cells derived from cord blood via Myostar catheter into the Endocardium in the area of the LAD. Five (5) patients receive a similar volume of normal saline via Myostar catheter into the endocardium in the area of the LAD. Four (4) patients receive 40 mg of Lipitor and 81 mg of aspirin daily for 1 year. After 1 year the group that receives the stem cells has an average occlusion of 47% and average total cholesterol of 211. The group with the normal saline has an average occlusion of 50.4% and average total cholesterol of 223. The group with aspirin and Lipitor has an average total occlusion of 49.1% and average total cholesterol of 209. The physician managing the study decides to give the normal saline group an effective dose of stem cells derived from cord tissue by IV. Results are pending.

EXAMPLE 17

Eleven (11) diabetic patients with an average Hemoglobin A1c of 7.6 are experiencing TIA's. The patients are on Metformin 500 mg bid and aspirin 325 mg per day. Six (6) patients receive an effective does of stem cells derived from cord blood by IV. Five (5) patients receive a similar volume of normal saline by IV. All patients remain on their doses of metformin and aspirin. One month later only one patient in the stem cell treatment group has a TIA and the average A1c is 7.2. Four (4) patients in the normal saline group still have TIA's and the average A1c is 7.5.

EXAMPLE 18

Limb Ischemia: Twenty three (23) diabetic patients with critical limb ischemia were injected with intramuscular autologous peripheral blood mononuclear cells. Eight (8) patients with critical limb ischemia were injected intramuscularly with umbilical cord derived mesenchymal Cells. During follow up both groups showed improvement in lower limb rest pain and ulcers. The umbilical cord derived mesenchymal cell group showed improved blood flow and increased blood vessels as additional benefits.

EXAMPLE 19

Thirty eight (38) type I patients received their usual dose of insulin. Twenty (20) of those patients receive Immunosuppressive therapy and also hematopoietic stem cells by IV. Eighteen (18) of the stem cell treated patients have their Aic's lowered to below seven (7). All the remaining patients have Aic's that remain over seven (7). Further studies will be initiated comparing stem cells derived from cord blood to these stem cells.

What is claimed is:

1. A method for improving blood flow to prevent or treat ischemia, and/or prevent or treat disease by delivering stem cells, comprising the steps of:
   a) selecting a patient with at least 20% occlusion of at least one of external carotid arteries, internal carotid arteries, cerebral arteries, or coronary arteries;
   b) administering at least one dose consisting of an effective amount of stem cells, wherein the stem cells are one or more of stem cells collected from umbilical cord blood, or cord tissue, Mesenchymal, Hematopoietic or bone marrow mononuclear cells., and wherein administration is intravenous (IV), intra thecal, intra-arterial, via catheter, via Myostar catheter into the heart, intracoronary, intrapericardial, or by direct injection into a heart and/or brain;
   c) monitoring the effectiveness of administration by a monitoring means that objectively measures blood flow and includes at least one of ultrasound, magnetic resonance angiogram and neuroimaging at selected time periods and determining if occlusion worsens by 2% or more;
   d) repeating steps b) and c) until there is at least one or clinical indication of: (i) prevention, lessening or delay of ischemia, (ii) prevention, lessening or delay in progression of arteriosclerosis, (iii) prevention, lessening or delay of autism, cerebral palsy, brain trauma and/or dementia, (iv) until there is improvement of the complication of ischemia, or (v) until there is contraindication to continued treatment, wherein repeat dose of stem cells, if administered, is administered by a method that is at least as invasive as the method utilized for the administration of the dose of stem cells in step b).

2. The method of claim 1 wherein monitoring means further comprises one or more invasive or non-invasive methods.

3. The method of claim 2 wherein the invasive method comprises angiogram.

4. The method of claim 2 wherein the noninvasive method comprises at least one of carotid ultrasound, transcranial ultrasound, MRA, Spectscan, functional neuroimaging, or nuclear stress testing.

5. The method of claim 1 wherein the selected time period for determining the effectiveness of administration is monthly.

6. The method of claim 1 wherein the selected time period for determining the effectiveness of administration is quarterly.

7. The method of claim 1 wherein the selected time period for determining the effectiveness of administration is semi-annually.

8. The method of claim 1 wherein the selected time period for determining effectiveness of administration is yearly.

9. The method of claim 1 wherein the method is used to reduce appearance of aging.

10. The method of claim 1, wherein the stem cells are autologous.

11. The method of claim 1, wherein the cells are allogenic and if clinically indicated from an HLA matched individual.

12. A method for improving blood flow to prevent or treat ischemia, and/or prevent or treat disease by delivering stem cells derived from cord blood and/or tissue, comprising the steps of:
   a) selecting a patient with decreased perfusion as evidenced by one or more selected indicators determined after adequate fluid intake, wherein the indicators comprise at least one of: i) blood pressure less than 97/65, ii) pulse less than 49, iii) ejection fraction less than 49%, or iv) cardiac output less than 3.7;
   b) administering at least one dose consisting of an effective amount of stem cells, wherein the stem cells are one or more of stem cells collected from umbilical cord blood, or cord tissue, Mesenchymal Hematopoietic or bone marrow mononuclear cells, and wherein administration is intravenous (IV), intra thecal, intra-arterial, via catheter, via Myostar catheter into the heart, intracoronary, intrapericardial, or by direct injection into a brain and/or heart,
   c) monitoring the effectiveness of administration by a monitoring means that objectively measures blood flow and includes at least one of ultrasound, magnetic resonance angiogram and neuroimaging at selected time periods and repeating b) until the one or more selected perfusion indicators shows an improvement selected from at least one of: i) BP is at least 119/79; ii) pulse is at least 59; iii) ejection fraction is at least 54%; or iv) cardiac output is at least 3.9, or until there is contraindication to continued treatment, wherein the repeat dose of stem cells, if administered, is administered by a method that is at least as invasive as the method utilized for the administration of the dose of stem cells in b).

13. The method of claim 12, wherein the stem cells are autologous.

14. The method of claim 12, wherein the stem cells are allogenic and if clinically indicated HLA matched.

15. A method for improving blood flow to prevent or treat ischemia, and/or prevent or treat disease by delivering stem cells, comprising the steps of:
   a) selecting a patient with at least 15% occlusion of peripheral arteries by invasive or noninvasive methods;
   b) administering at least one dose consisting of an effective amount of stem cells, wherein the stem cells are one or more of stem cells collected from cord blood, or cord tissue, Mesenchymal, Hematopoietic or bone marrow mononuclear cells, and wherein administration is by IV, intra-arterial, via a catheter into, or by direct injection into a leg muscle;

c) monitoring monthly, quarterly, semiannually, or yearly by the invasive or noninvasive methods above;

d) if the monitoring in c) shows that the occlusion worsens by 2% or more, or the ABI is worse by at least 0.02 repeating b) and c) to continue to: (i) prevent, lessen or delay ischemia; (ii) prevent, lessen or delay the progression of arteriosclerosis, (iii) prevent or lessen or delay the complications of ischemia, or (iv) until there is contraindication to continued treatment;

e) optionally repeating b) and c) earlier than 1 month after the cell administration if there are complications of ischemia, comprising one or more of worsening or severe claudication, critical limb ischemia, risk of amputation, leg muscle death; and f) optionally if monitoring shows no improvement repeat steps b) and c) until there is improvement of claudication, critical limb ischemia, risk of amputation, and or leg muscle death or until there is contraindication to continued treatment.

16. The method of claim 15 wherein the at least 15% occlusion of peripheral arteries is determined by one or more invasive methods comprising angiogram.

17. The method of claim 15 wherein the at least 15% occlusion of peripheral arteries is determined by one or more noninvasive methods comprising Ankle-brachial index is less than or equal to 0.85.

18. The method of claim 15, wherein the stem cells are autologous.

19. The method of claim 15, wherein the stem cells are allogenic and if clinically indicated HLA matched.

20. A method for preventing or treating ischemia for preventing or managing disease by delivering stem cells, consisting of:

a) selecting a patient at risk for or suffering from a condition caused in at least some part by ischemia or at risk for ischemia;

b) administering at least one dose consisting of an effective amount of stem cells, wherein the stem cells are one or more of stem cells collected from umbilical cord blood or cord tissue, Mesenchymal, Hematopoietic, or bone marrow mononuclear cells, and wherein administration is intravenous (IV), intra-arterial, via catheter, via Myostar catheter into the heart, intracoronary, intrapericardial, or by direct injection into a heart, leg muscle and/or pancreas;

c) monitoring the effectiveness of administration of said stem cells by a monitoring means that objectively measures blood flow and/or organ dysfunction and includes at least one of MRA, Angiogram, ABI, Doppler, Spectcsan, Functional Neuroimaging, Nuclear Stress Testing, Carotid Ultrasound, Transcranial Ultrasound, Ultrasound, Cardiac Echo, Stress Echo, MRI, EEG, EKG,EMG, Cat Scan, blood tests;

d) determining, based on monitoring the effectiveness of stem cell treatment by said monitoring means, whether an additional dose of stem cells is indicated; and e) if indicated, repeating steps b) through d) until there is a clinical indication of improvement, or until there is contraindication to continued treatment; wherein the second dose of stem cells, if administered, is administered by a method that is at least as invasive as the method utilized for the administration of the previous dose of stem cells.

21. The method of claim 20 wherein the condition disease is at least one of, arteriosclerosis, autonomic neuropathy, aging, complications of diabetes type 1,or complications of diabetes type 2.

22. The method of claim 21 further comprising collecting umbilical cord blood and/or tissue to derive stem cells.

23. The method of claim 22, wherein said blood tests include determination of hemoglobin A1c levels.

24. The method of claim 20, wherein the patients receive Immunosuppressive therapy.

25. The method of claim 20, wherein the stem cells are autologous.

26. The method of claim 20, wherein the stem cells are allogenic and if clinically indicated HLA matched.

27. The method of claim 21 wherein the one or more of stem cells collected from umbilical cord blood, cord tissue, Mesenchymal, Hematopoietic or bone marrow mononuclear cells are administered to reduce the complications of diabetes type 1 or 2.

28. A method for preventing or treating ischemia for preventing or managing disease by delivering stem cells, consisting of:

a) selecting a patient at risk for or suffering from a condition caused in at least some part by ischemia or at risk for ischemia, wherein the condition is autism, cerebral palsy, brain trauma, dementia, and/or stroke;

b) administering at least one dose consisting of an effective amount of stem cells, wherein the stem cells are one or more of stem cells collected from Mesenchymal, Hematopoietic, or bone marrow mononuclear cells, and wherein administration is intravenous (IV), intrathecal, intra-arterial, via catheter, via Myostar catheter into the heart, intracoronary, intrapericardial, or by direct injection into a heart, brain, leg muscle and/or pancreas;

c) monitoring the effectiveness of administration of said stem cells by a monitoring means that objectively measures blood flow and/or organ dysfunction and includes at least one of MRA, Angiogram, ABI, Doppler, Spectcsan, Functional Neuroimaging, Nuclear Stress Testing, Carotid Ultrasound, Transcranial Ultrasound, Ultrasound, Cardiac Echo, Stress Echo, MRI, EEG, EKG,EMG, Cat Scan, blood tests;

d) determining, based on monitoring the effectiveness of stem cell treatment by said monitoring means, whether an additional dose of stem cells is indicated; and e) if indicated, repeating steps b) through d) until there is a clinical indication of improvement, or until there is contraindication to continued treatment; wherein the second or subsequent dose of stem cells, if administered, is administered by a method that is at least as invasive as the method utilized for the administration of the previous dose of stem cells.

* * * * *